US009943499B2

(12) United States Patent
Singh

(10) Patent No.: US 9,943,499 B2
(45) Date of Patent: Apr. 17, 2018

(54) LIPASE INHIBITORS FOR THE TREATMENT OF PANCREATITIS AND ORGAN FAILURE

(71) Applicant: UNIVERSITY OF PITTSBURGH—OF THE COMMONWEALTH SYSTEM OF HIGHER EDUCATION, Pittsburgh, PA (US)

(72) Inventor: Vijay Prem Singh, Scottsdale, AZ (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 16 days.

(21) Appl. No.: 14/677,770

(22) Filed: Apr. 2, 2015

(65) Prior Publication Data
US 2015/0283109 A1 Oct. 8, 2015

Related U.S. Application Data

(62) Division of application No. 13/447,850, filed on Apr. 16, 2012, now Pat. No. 9,023,887.

(60) Provisional application No. 61/476,119, filed on Apr. 15, 2011.

(51) Int. Cl.
*A61K 31/337* (2006.01)
*A61K 31/536* (2006.01)

(52) U.S. Cl.
CPC .......... *A61K 31/337* (2013.01); *A61K 31/536* (2013.01)

(58) Field of Classification Search
None
See application file for complete search history.

(56) References Cited

U.S. PATENT DOCUMENTS

2007/0060532 A1 3/2007 Junien et al.

OTHER PUBLICATIONS

Lunagariya et al., "Inhibitors of Pancreatic Lipase: State of the Art and Clinical Perspectives", EXCLI Journal, 2014, vol. 13, pp. 897-921.*
U.S. Appl. No. 13/447,850 (U.S. Pat. No. 9,023,887), filed Apr. 16, 2012 (May 5, 2015).
U.S. Appl. No. 13/447,850, Mar. 18, 2015 Issue Fee Payment.
U.S. Appl. No. 13/447,850, Dec. 19, 2014 Notice of Allowance.
U.S. Appl. No. 13/447,850, Sep. 8, 2014 Response to Non-Final Office Action.
U.S. Appl. No. 13/447,850, Apr. 7, 2014 Non-Final Office Action.
U.S. Appl. No. 13/447,850, Dec. 23, 2013 Response to Restriction Requirement.
U.S. Appl. No. 13/447,850, Nov. 25, 2013 Restriction Requirement.

Aho et al., "Experimental Pancreatitis in the Rat: Ultrastructure of Sodium Taurocholate-Induced Pancreatic Lesions," Scand. J. Gastroent., 15(4):417-424 (1980).
Anderson et al., "Peroxidise Linoleic Acid and Experimental Pancreatitis," International Journal of Pancreatology, 1:237-248 (1986).
Bryson et al., "Reduction of Dietary Fat Absorption by the Novel Gastrointestinal Lipase Inhibitor Cetilistat in Healthy Volunteers," British Journal of Clinical Pharmacology, 67(3):309-315 (2009).
Ciesla et al., "Obesity Increases risk of Organ Failure After Severe Trauma," Journal of American College of Surgeons, 203:539-545 (2006).
Dettelbach et al., "Intraperitoneal Free Fatty Acids Induce Severe Hypocalcemia in Rats: A Model for the Hypocalcemia of Pancreatitis," Journal of Bone and Mineral Research, 5(12):1249-1255 (1990).
Everhart et al., "Burden of digestive Diseases in the United States Part I: Overall and Upper Gastrointestinal Diseases," Gastroenterology, 136:376-386 (2009).
Funnell et al., "Obesity: An Important Prognostic Factor in Acute Pancreatitis," Br. J Surg., 80:484-486 (1993).
Ghanem et al., "Body Mass Index (BMI) and Mortality in Patients with Severe Burns: Is There a "tilt Point" at Which Obesity Influences Outcome?", Burns, 37:208-214 (2011).
Ghanim et al., "Circulating Mononuclear Cells in the Obese Are in a Proinflammatory State," Circulation, 110:1564-1571 (2004).
Hagenfeldt, "Renal Excretion of Free Fatty Acids," Clinica Chimica Acta, 32:471-474 (1971).
Heiss et al., "Severe Acute Pancreatitis Requiring Drainage Therapy: Findings on Computed Tomography as Predictor of Patient Outcome," Pancreatology, 10(6):727-733 (2010).
Hussain et al., "Neutrophil Apoptosis During the Development and Resolution of Oleic Acid-Induced Acute Lung Injury in the Rat," Am. J. Respir. Cell Mol. Biol., 19:867-874 (1998).
Ibrahim, "Subcutaneous and Visceral Adipose Tissue: Structural and Functional Differences," Obesity Reviews, 11:11-18 (2010).
Ishola et al., "Albumin-Bound Fatty Acids Induce Mitochondrial Oxidant Stress and Impair Antioxidant Responses in Proximal Tubular Cells," Kidney International, 70:724-731 (2006).
Jeschke et al., "Insulin Treatment Improves the Systemic Inflammatory Reaction to Severe Trauma," Annals of Surgery, 239(4):553-560 (2004).
Johnson et al., "Combination of APACHE-II Score and an Obesity Score (APACHE-0) for the Prediction of Severe Acute Pancreatitis," Pancreatology, 4:1-6 (2004).
Karimgani et al., "Prognostic Factors in Sterile Pancreatic Necrosis," Gastoenterology, 103:1636-1640 (1992).

(Continued)

*Primary Examiner* — Savitha M Rao
*Assistant Examiner* — Gregg Polansky
(74) *Attorney, Agent, or Firm* — Baker Botts LLP

(57) ABSTRACT

The present invention relates to methods for treating pancreatitis and/or organ failure comprising administering, to a subject in need of such treatment, an effective amount of a lipase inhibitor. It is based, at least in part, on the discoveries that lipotoxicity contributes to inflammation, multisystem organ failure, necrotic pancreatic acinar cell death and in acute pancreatitis, and that inhibition of lipolysis was able to reduce indices associated with these conditions. Accordingly, in various embodiments, the present invention provides for methods and compositions for limiting lipotoxicity and thereby reducing the likelihood of poor outcomes associated with acute pancreatitis and other severe systemic conditions, especially in obese individuals.

Figure 1:
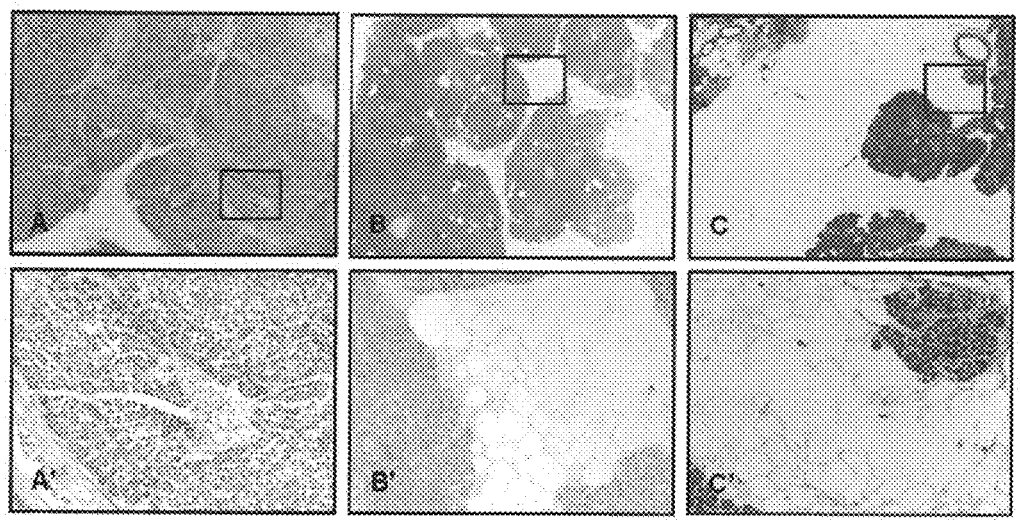

12 Claims, 40 Drawing Sheets
(15 of 40 Drawing Sheet(s) Filed in Color)

(56) References Cited

OTHER PUBLICATIONS

Kataoka et al., "Pathophysiologic Studies of Experimental Chronic Pancreatitis in Rats Induced by Injection of Zein-Oleic Acid-Linoleic Acid Solution into the Pancreatic Duct," Pancreas, 16(3):289-299 (1998).
Kimura et al., "Comparison of Different Treatment Modalities in Experimental Pancreatitis in Rats," Gastroenterology, 103 (6):1916-1924 (1992).
Klöppel et al., "Chronic Pancreatitis: Evolution of the Disease," Hepato-Gastroenterol, 38:408-412 (1991).
Klöppel et al., "Human Acute Pancreatitis: Its Pathogenesis in the Light of Immunocytochemical and Ultrastructural Findings in Acinar Cells," Virchows Arch [Pathol Anat], 409:791-803 (1986).
Klöppel et al., "Pseudocysts in Chronic Pancreatitis: A Morphological Analysis of 57 Resection Specimens and 9 Autopsy Pancreata," Pancreas, 6(3):266-274 (1991).
Malinoski et al., "Elevated Serum Pancreatic Enzyme Levels After Hemorrhagic Shock Predict Organ Failure and Death," The Journal of Trauma Injury, Infection, and Critical Care, 67(3):445-449 (2009).
Martinez et al., "Obesity Is a Definitive Risk Factor of Severity and Mortality in Acute Pancreatitis: An Updated Meta-Analysis," Pancreatology, 6:206-209 (2006).
Martinez et al., "Obesity: A Prognostic Factor of Severity in Acute Pancreatitis," Pancreas, 19(1):15-20 (1999).
Mathur et al., "Nonalcoholic Fatty Pancreas Disease," HPB, 9:312-318 (2007).
Matsumoto et al., "Uneven Fatty Replacement of the Pancreas: Evaluation with CT1," Radiology, 194:453-458 (1995).
Mery et al., "Android Fat distribution as Predictor of Severity in Acute Pancreatitis," Pancreatology, 2:543-549 (2002).
Navina et al., "Lipotoxicity Causes Multisystem Organ Failure and Exacerbates Acute Pancreatitis in Obesity," Science Translational Medicine, 3:107ra110 (2011).
Oliveros et al., "Obesity and Mortality in Critically Ill Adults: A Systematic Review and Meta-Analysis," Obesity, 16:515-521 (2008).
Olsen, "Lipomatosis of the Pancreas in Autopsy Material and Its Relation to Age and Overweight," Acta Path. Microbial. Scand Sect. A., 86:367-373 (1978).
Padwal, "Cetilistat, A New Lipase Inhibitor for the Treatment of Obesity," Current Opinion in Investigational Drugs, 9(4):414-421 (2008).
Papachristou et al., "Obesity Increases the Severity of Acute Pancreatitis: Performance of APACHE-0 Score and Correlation with the Inflammatory Response," Pancreatology, 6:279-285 (2006).
Park et al., "Visceral Adipose Tissue Area is an Independent Risk Factor for Hepatic Steatosis," Journal of Gastroenterology and Hepatology, 23:900-907 (2008).
Paye et al., "Role of Nonesterified Fatty Acids in Necrotizing Pancreatitis: An In Vivo Experimental Study in Rats," Pancreas, 23(4):341-348 (2001).
Pini et al., "Effect of Diet-Induced Obesity on Acute Pancreatitis Induced by Administration of Interleukin-12 Plus Interleukin-18 in Mice," Obesity (Silver Spring), 18(3):476-481 (2010).
Porter et al., "Obesity as a Predictor of Severity in Acute Pancreatitis," Int. J. Pancreatol., 10:247-252 (1991).
Rosso et al., "The Role of "Fatty Pancreas" and of BMI in the Occurrence of Pancreatic Fistula After Pancreaticoduodenectomy," J Gastrointest Surg., 13:1845-1851 (2009).
Saisho et al., "Pancreas Volumes in Humans From Birth to Age One Hundred Taking Into Account Sex, Obesity, and Presence of Type-2 Diabetes," Clinical Anatomy, 20:933-942 (2007).
Schaffler et al., "Admission Resistin Levels Predict Peripancreatic Necrosis and Clinical Severity in Acute Pancreatitis," Am. J. Gastroenterol, 105(11):2474-2484 (2010).
Schmitz-Moormann et al., "Comparative Radiological and Morphological Study of the Human Pancreas," Path. Res. Pract., 171:325-335 (1981).
Schmitz-Moormann et al., "Lipomatosis of the Pancreas," Path. Res. Pract., 173:45-53 (1981).
Sempere et al., "Obesity and Fat distribution Imply a Greater Systemic Inflammatory Response and a Worse Prognosis in Acute Pancreatitis," Pancreatology, 8:257-264 (2008).
Sennello et al., "Interleukin-18, Together with Interleukin-12, Induces Severe Acute Pancreatitis in Obese but not in Nonobese Leptin-Deficient Mice," PNAS, 105(23):8085-8090 (2008).
Singh, "Obesity and Severe Acute Pancreatitis: From Deathbed to Bench," Presentation at Yale University, (36 lecture slides) (Nov. 2010).
Sztefko et al., "Serum Free Fatty Acid Concentration in Patients with Acute Pancreatitis," Pancreatology, 1:230-236 (2001).
Tsai, "Is Obesity a Significant Prognostic Factor in Acute Pancreatitis?'," Digestive Diseases and Sciences, 43(1):2251-2254 (1998).
Willemer et al., "Tubular Complexes in Cerulein- and Oleic Acid-Induced Pancreatitis in rats: Glycoconjugate Pattern, Immunocytochemical, and Ultrastructural Findings," Pancreas, 2(6):669-675 (1987).
Zhu et al., "A Somatostatin Analogue in Protective Against Retrograde Bile Salt-Induced Pancreatitis in the Rat," Pancreas, 6(5):609-613 (1991).

* cited by examiner

FIGURE 1A-C

FIGURE 3A-C

FIGURE 5A-B
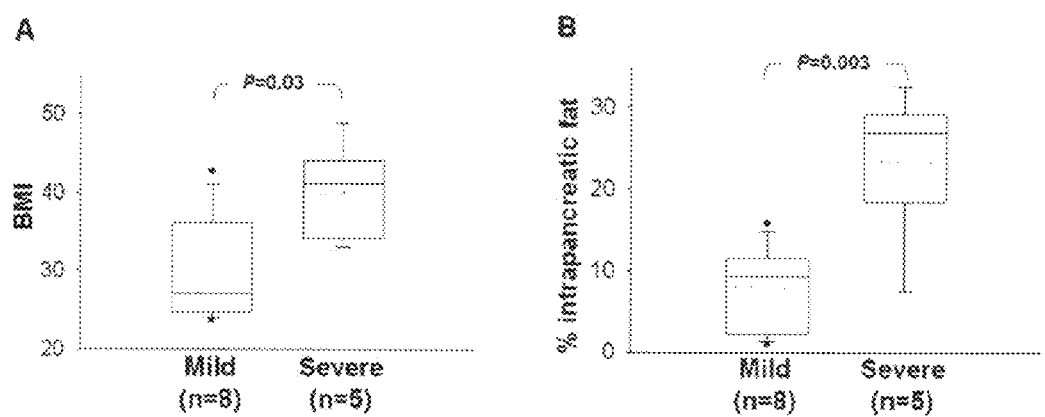

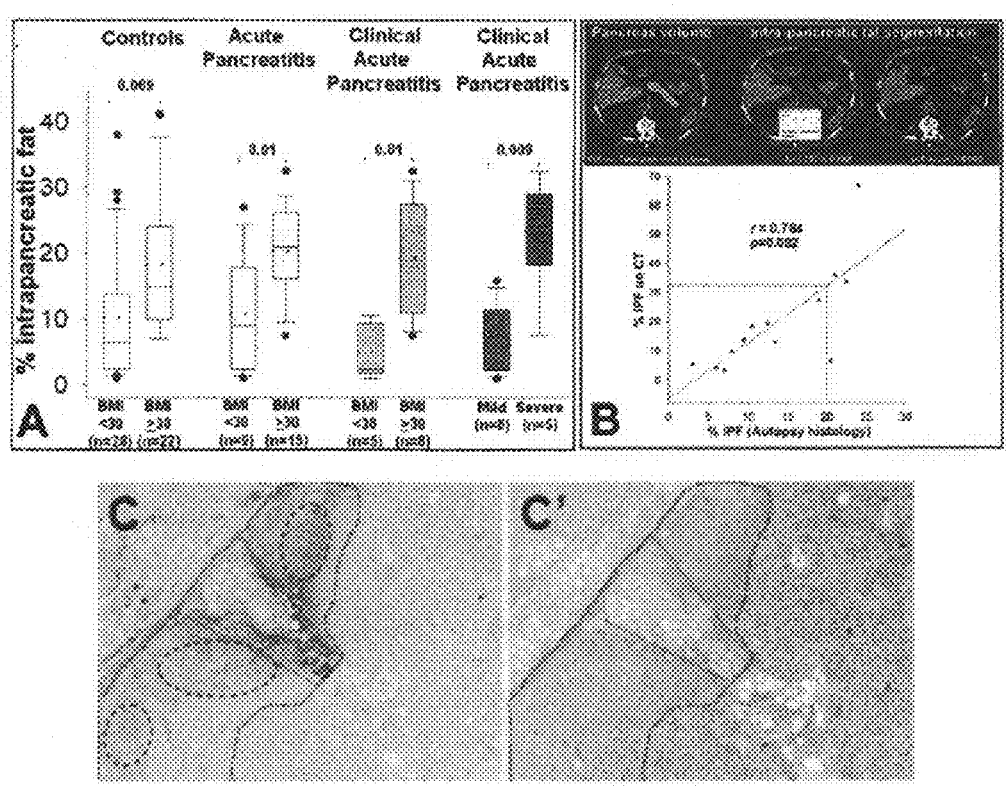
FIGURE 6A-C

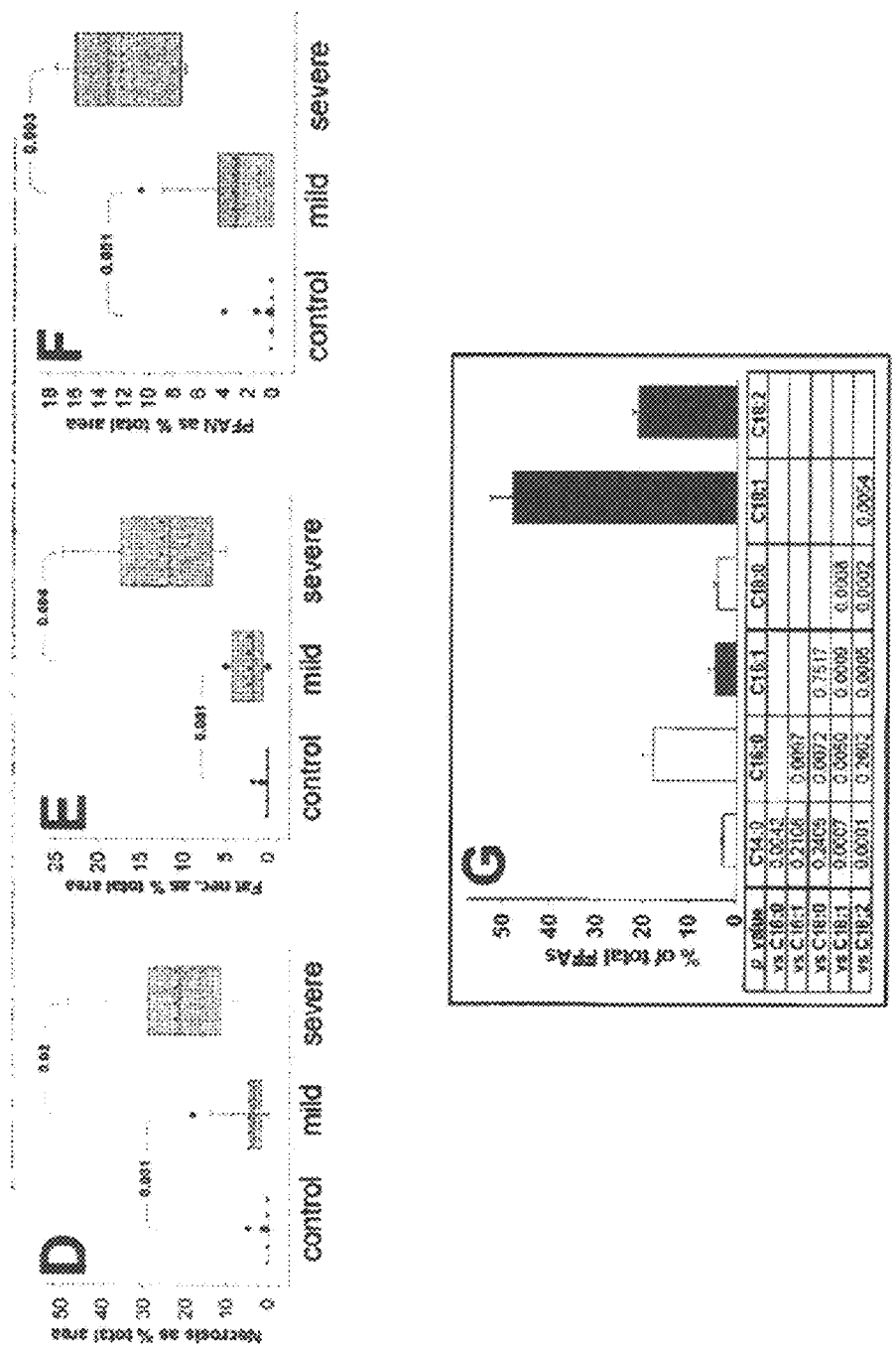

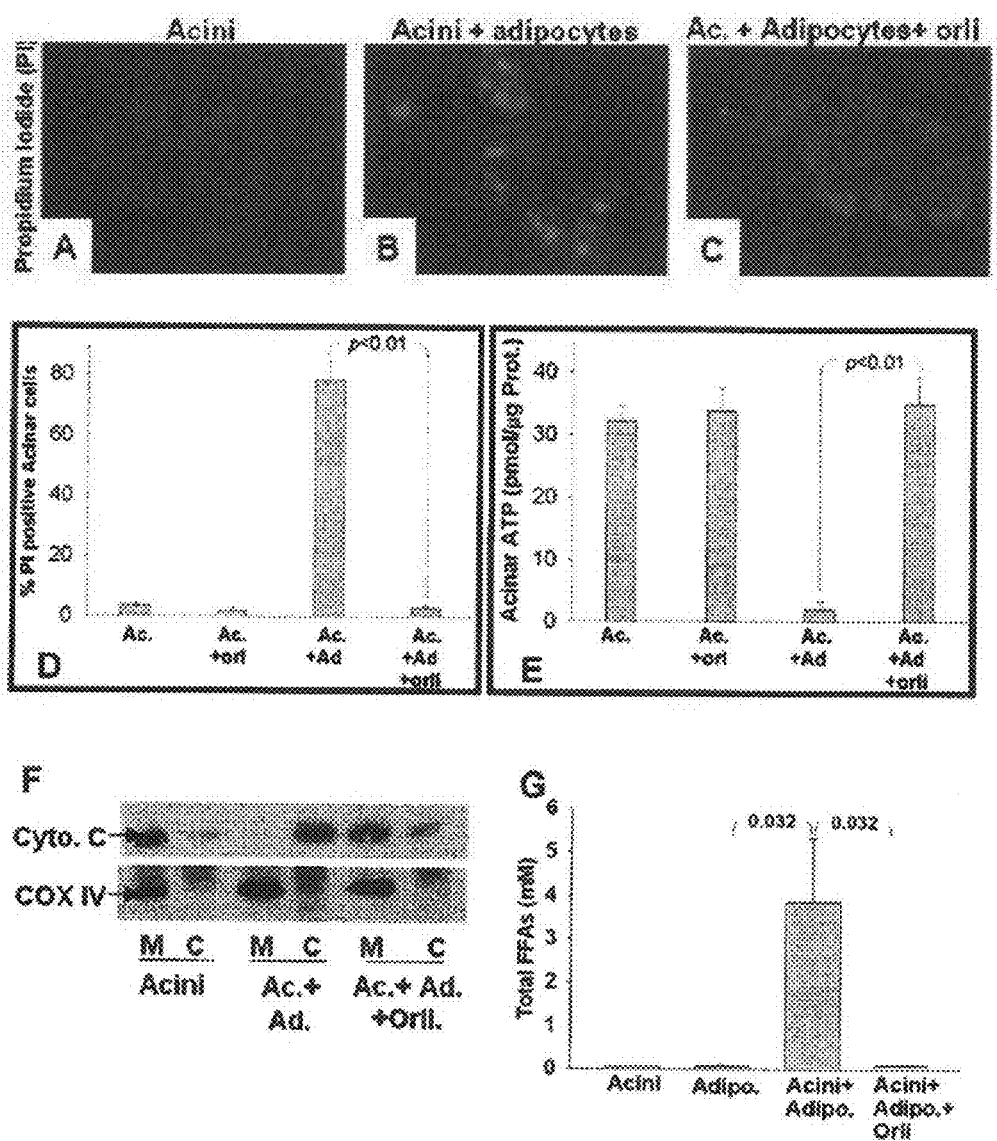
FIGURE 7A-G

FIGURE 8A-B
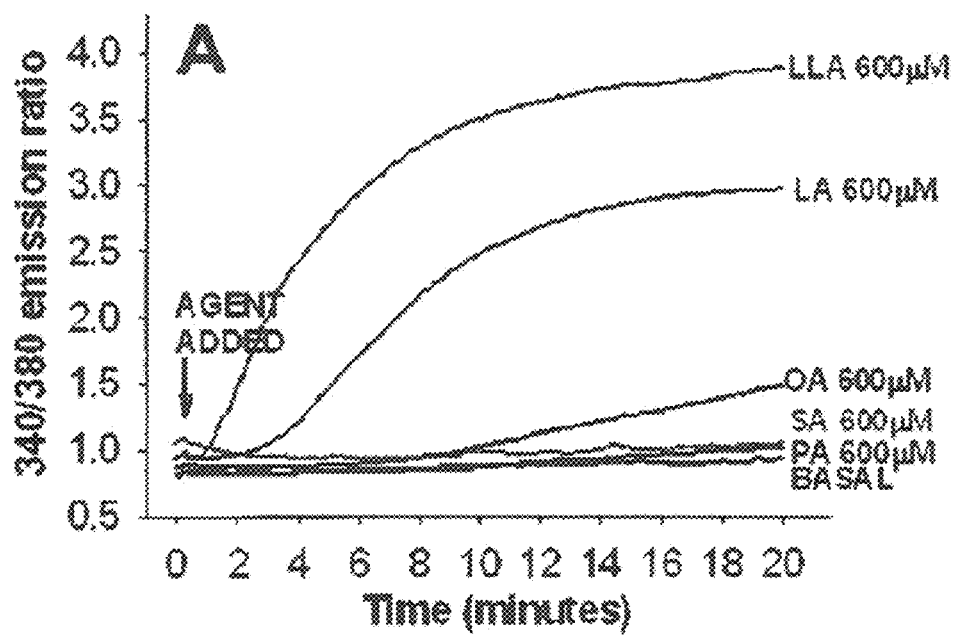
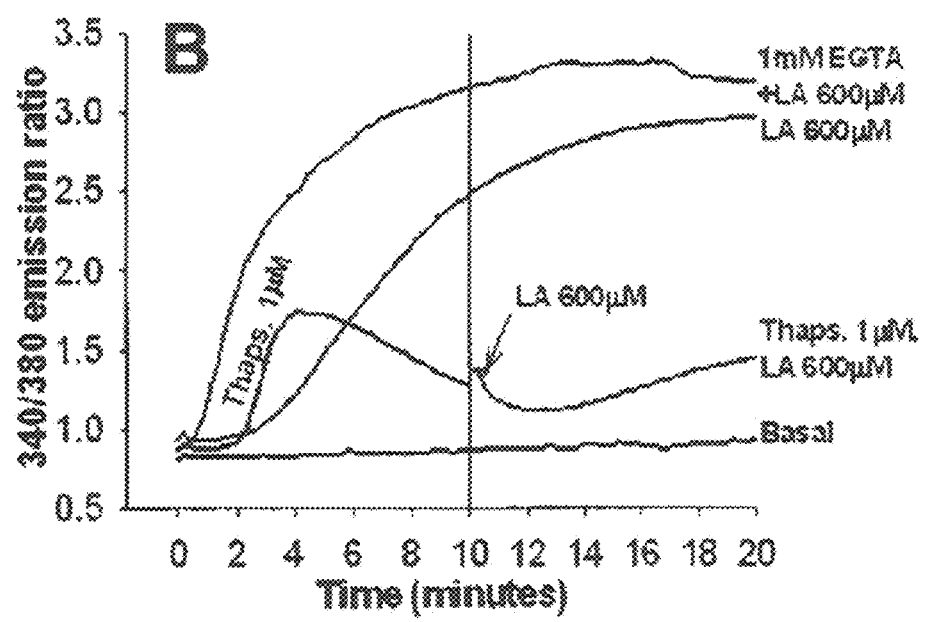

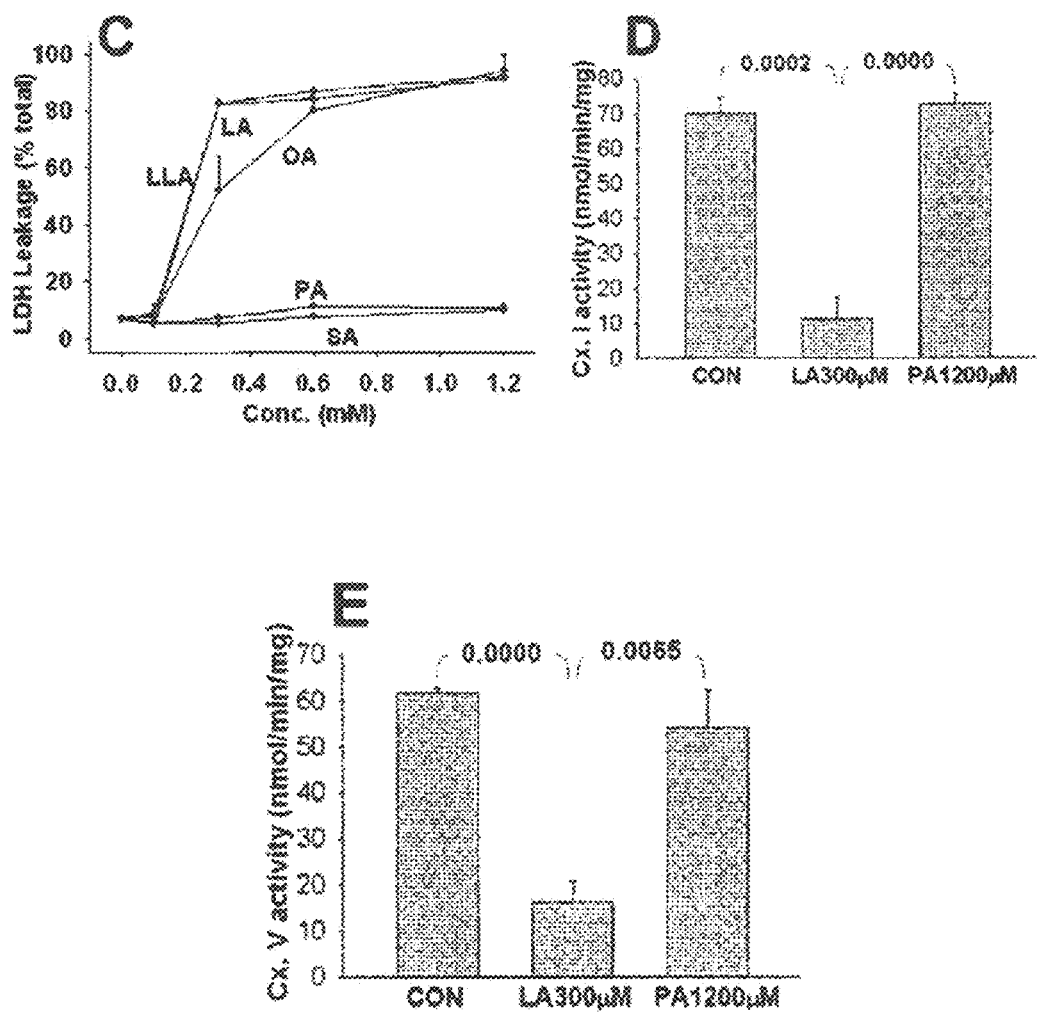
FIGURE 8C-E

FIGURE 8F-H
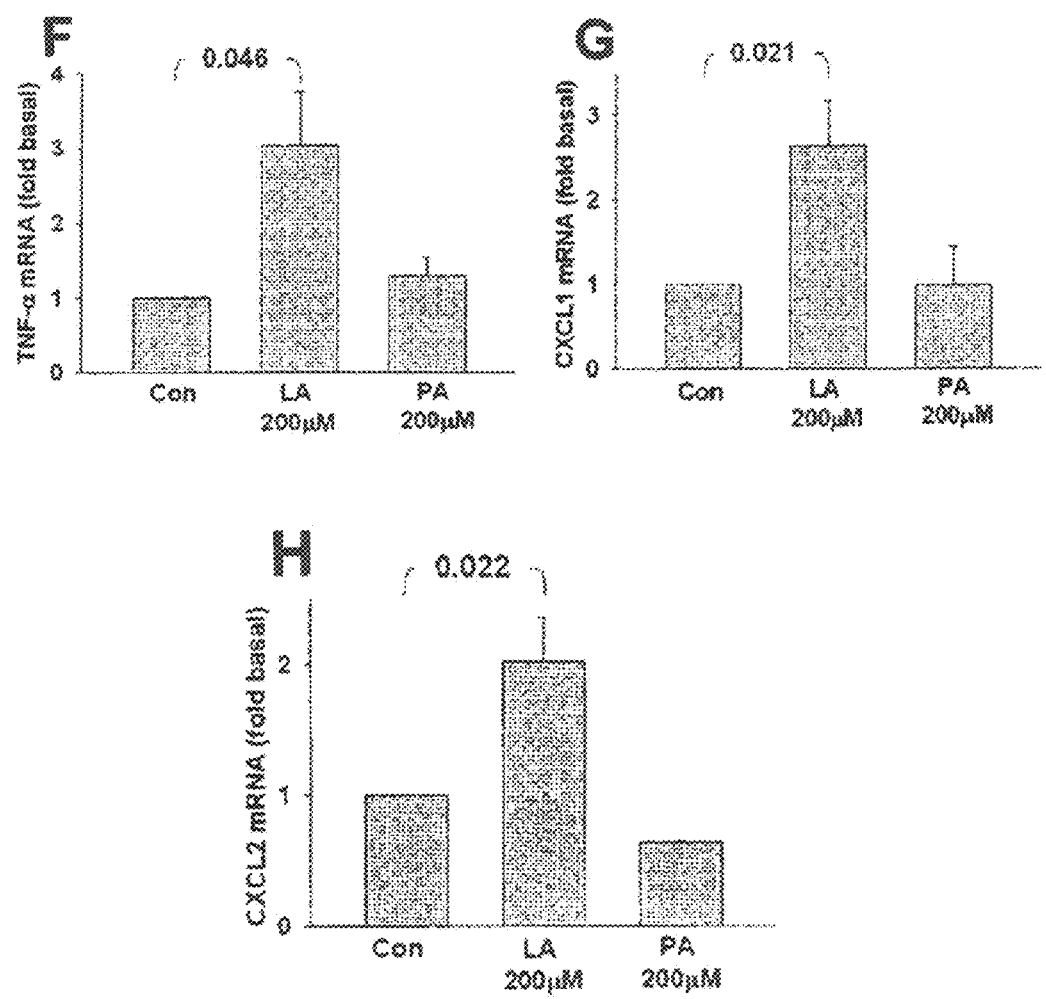

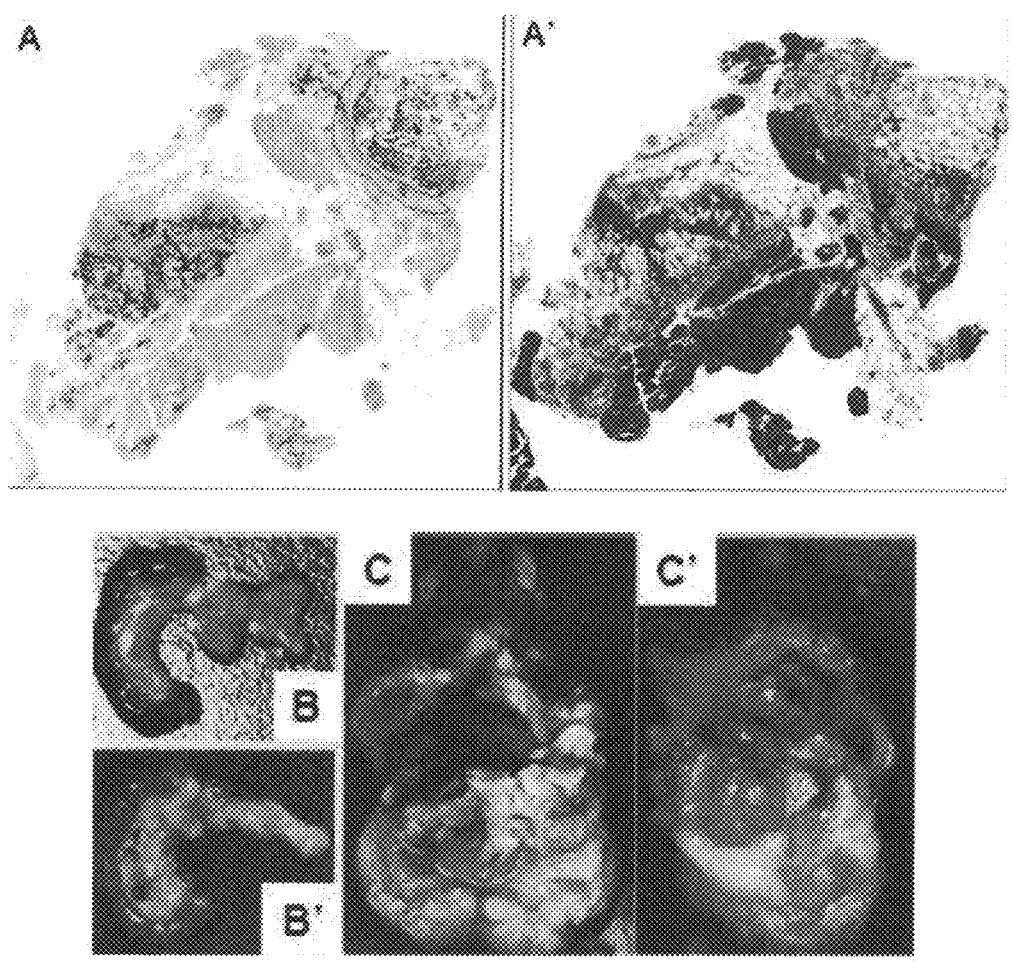
FIGURE 9A-C

FIGURE 9D-E
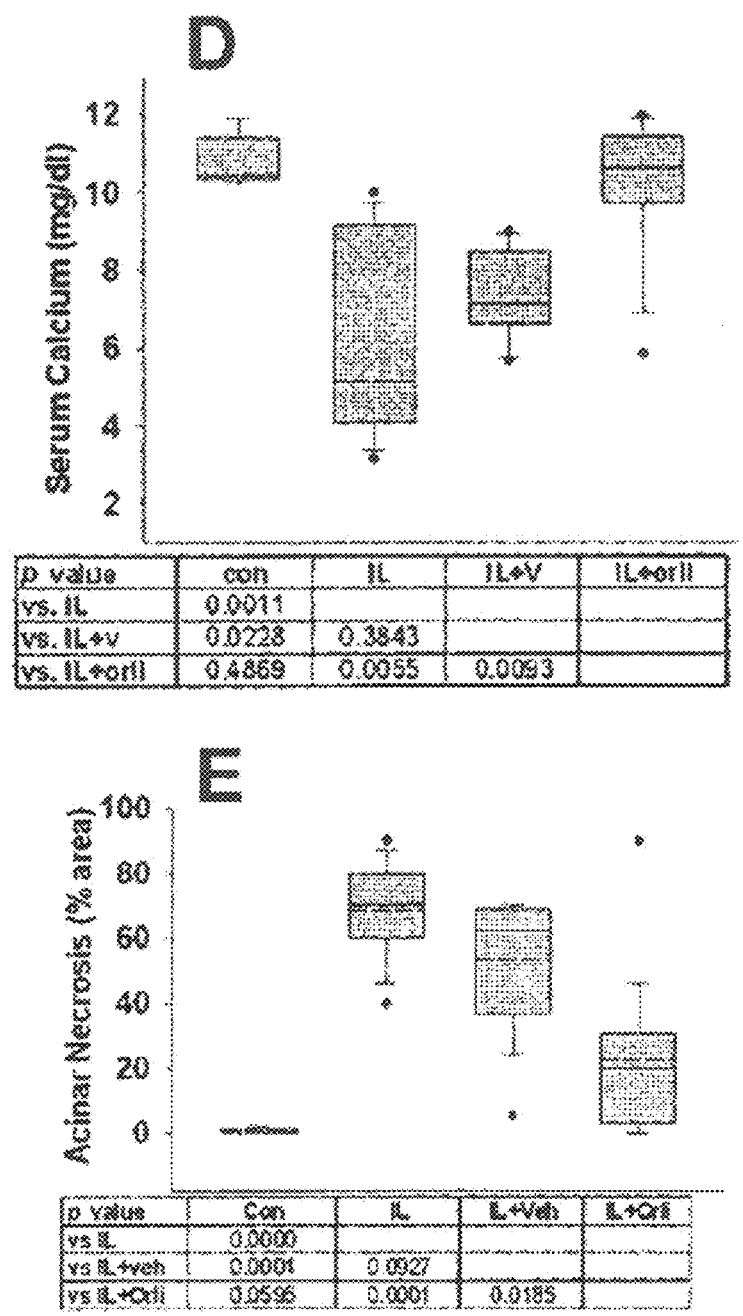

FIGURE 9F-G
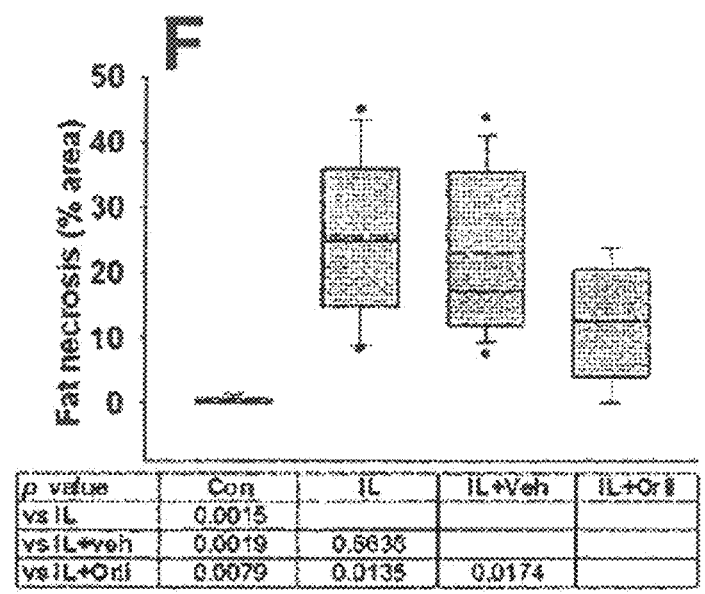
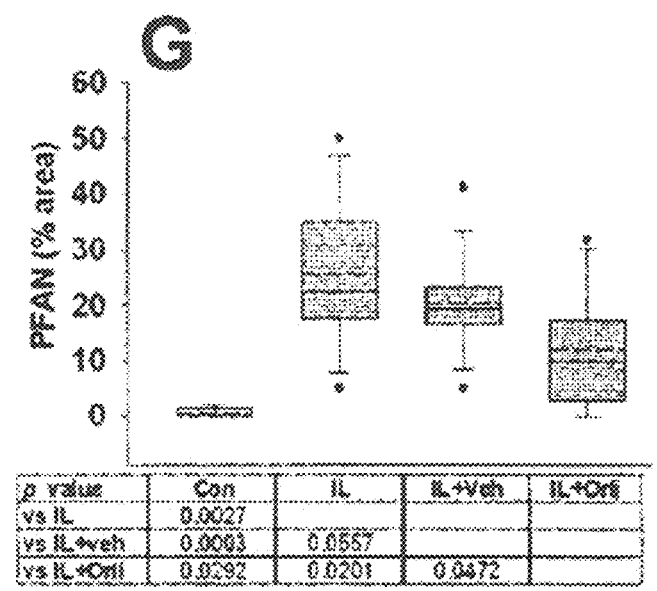

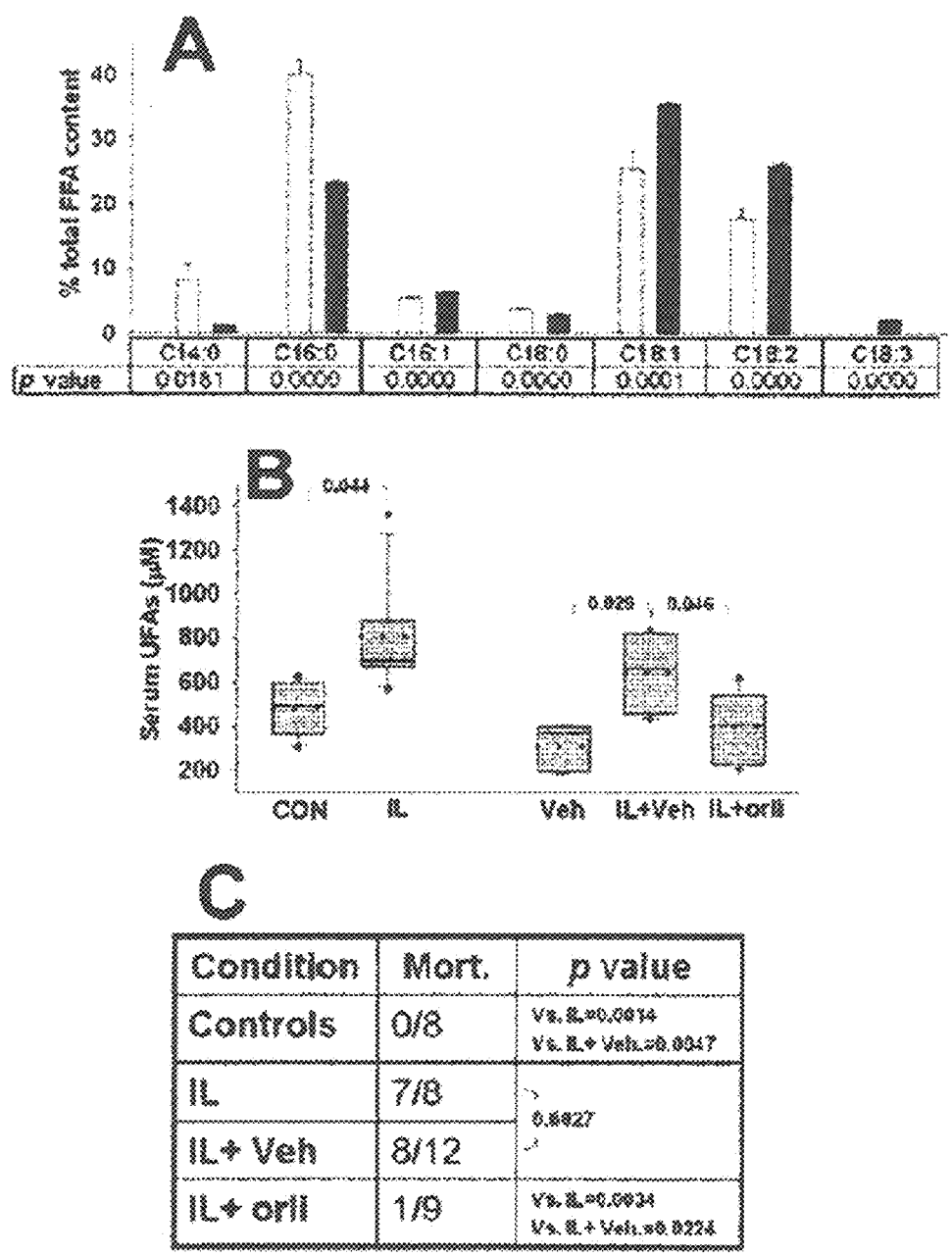
FIGURE 10A-C

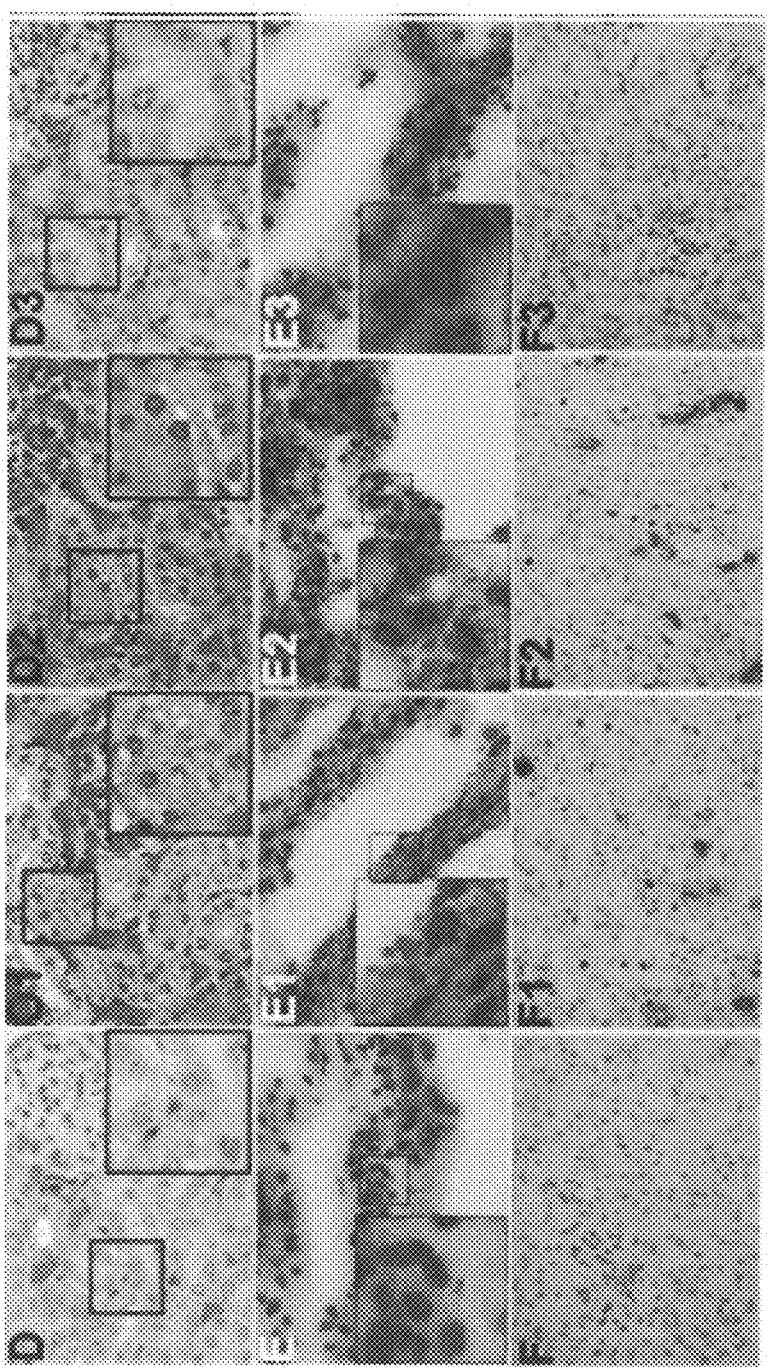
FIGURE 10D-F

FIGURE 10G-H
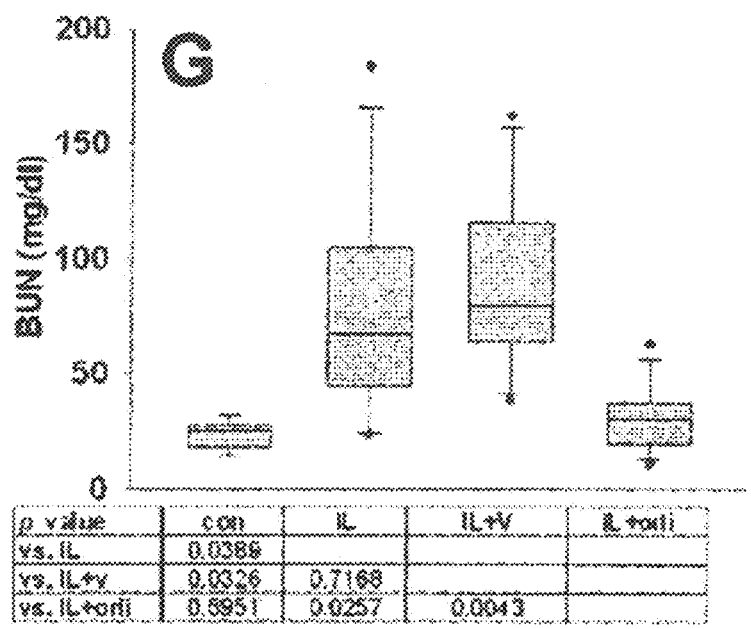
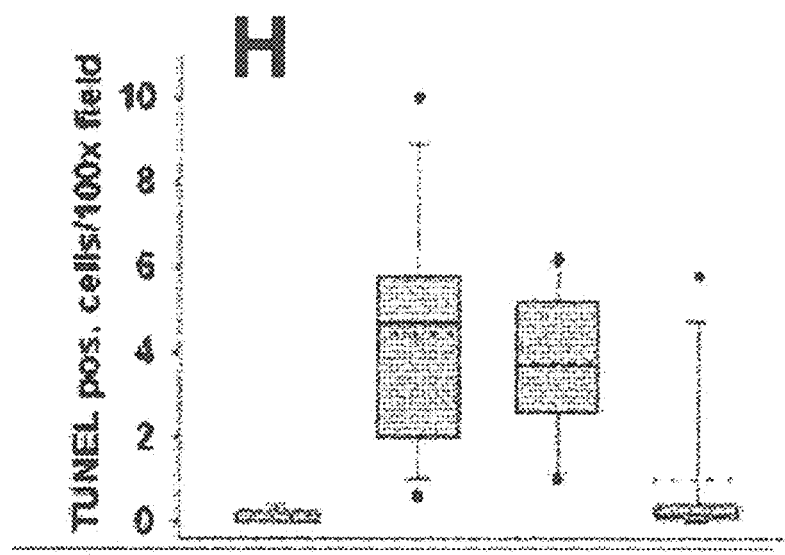

FIGURE 10I – J
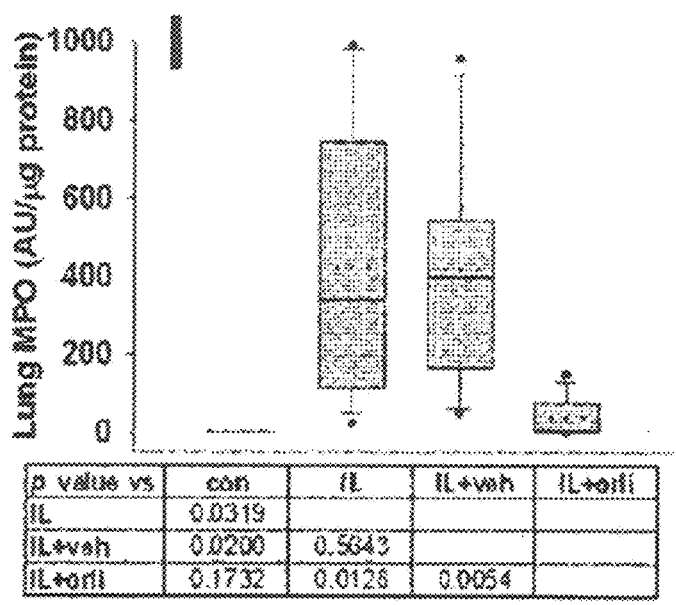
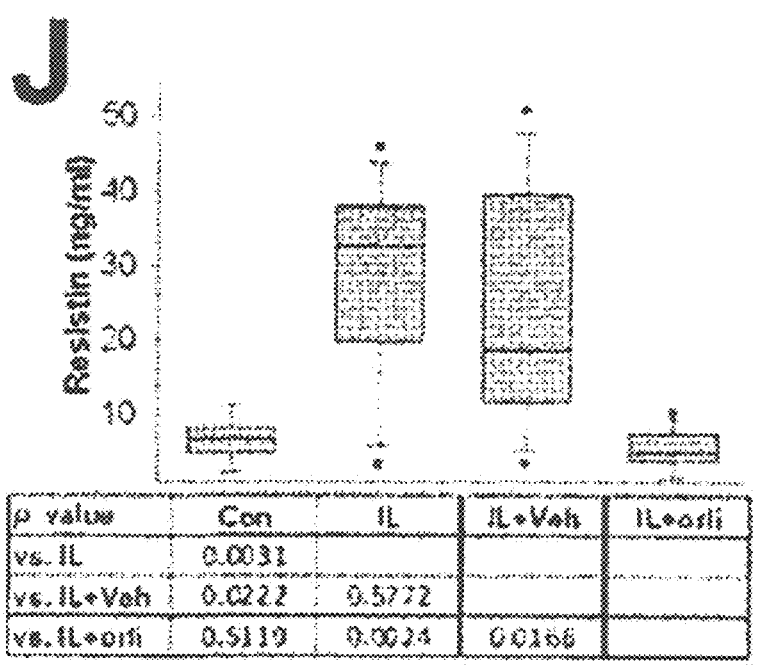

FIGURE 10K-L
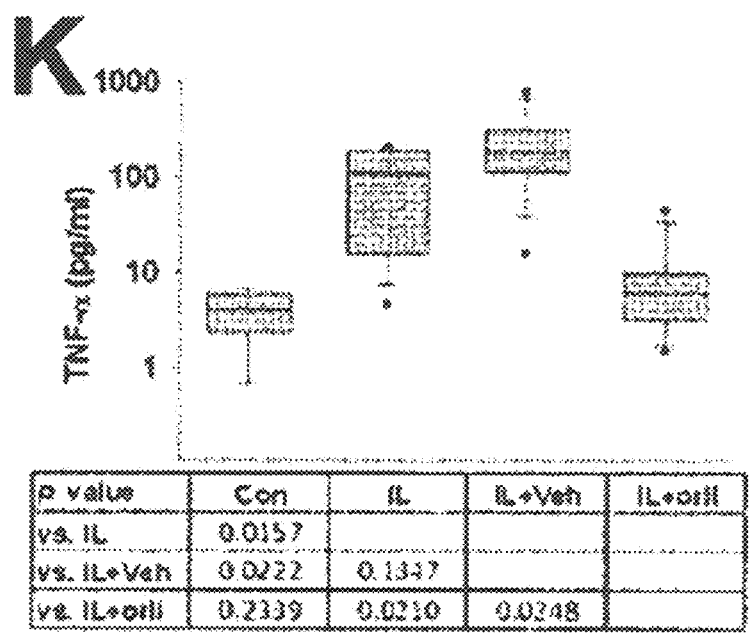
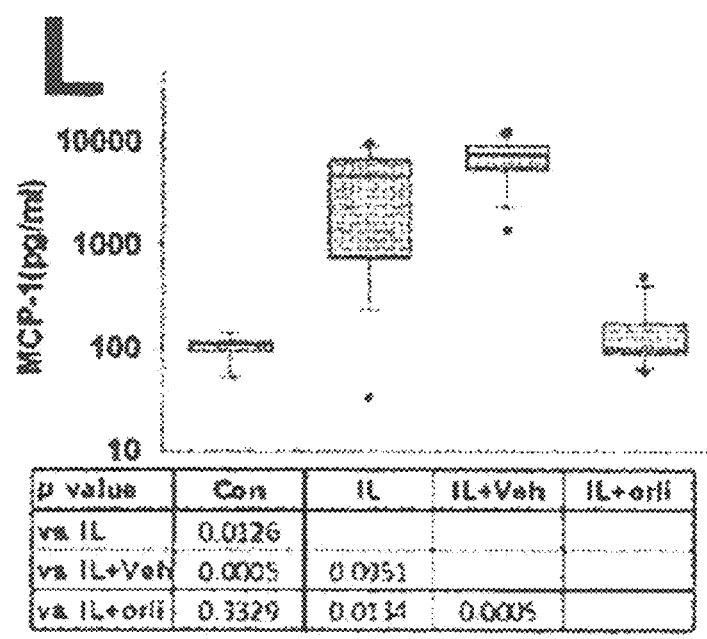

FIGURE 11A-B
A   Method 1: Average Hounsfield Units, from 3 regions of interest (head, body and tail)
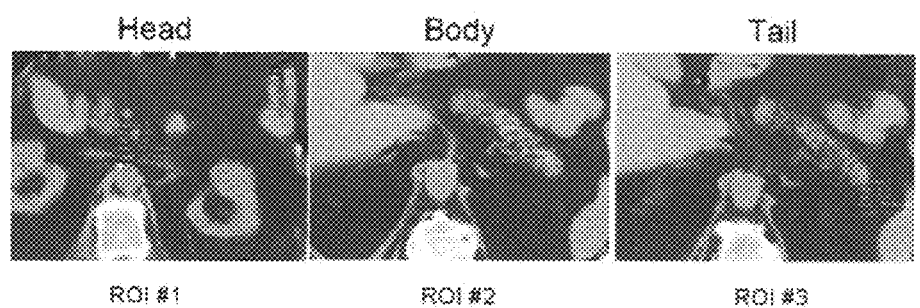
B   Corellation between %IPF on histology and mean pancreatic HU
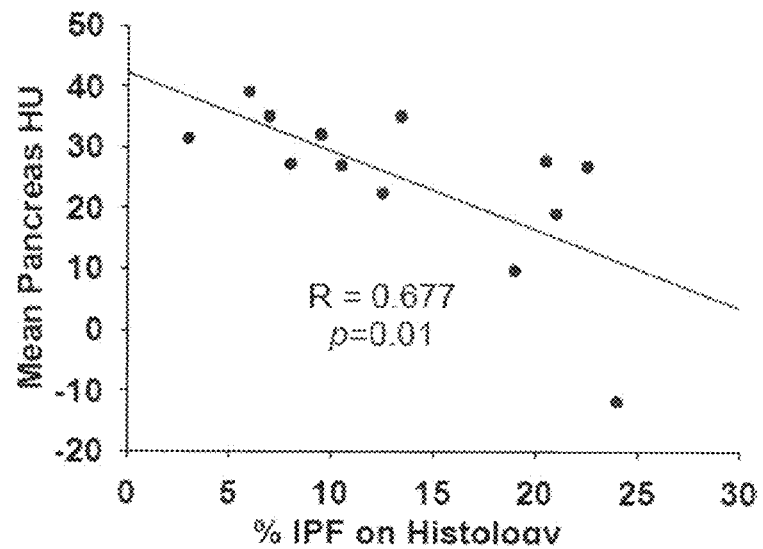

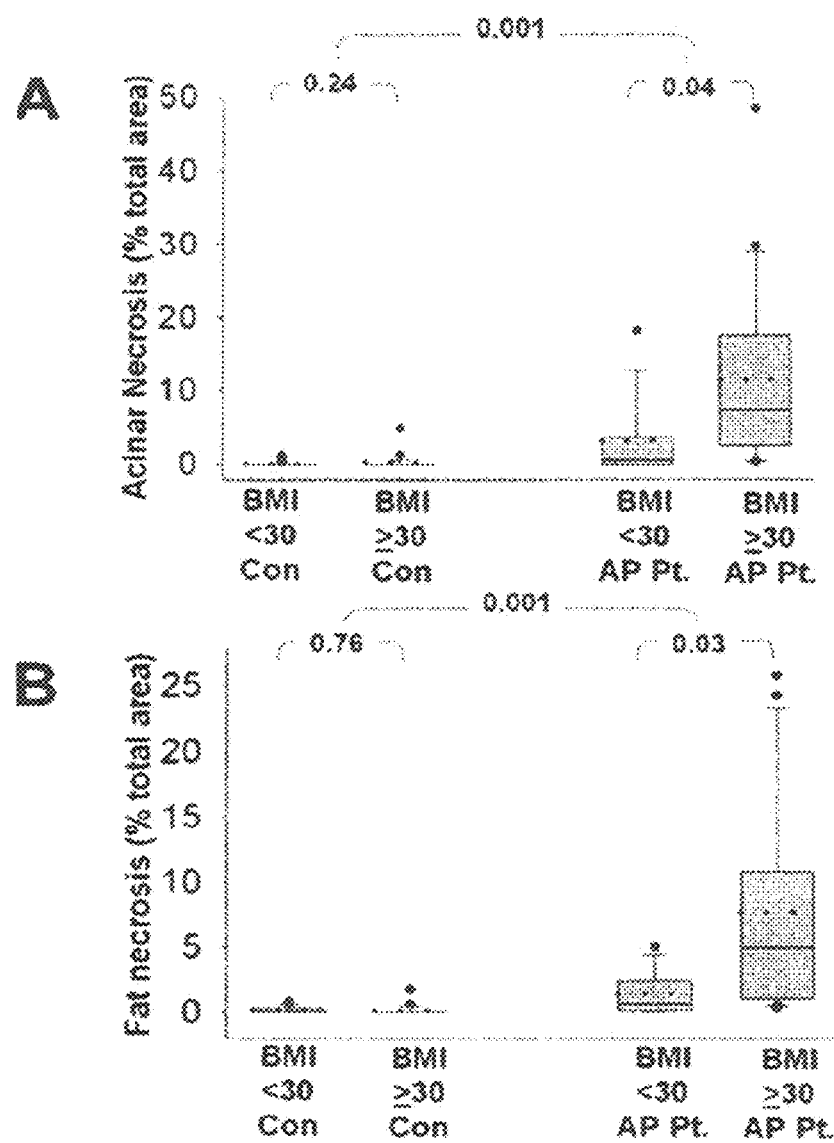
FIGURE 12A-B

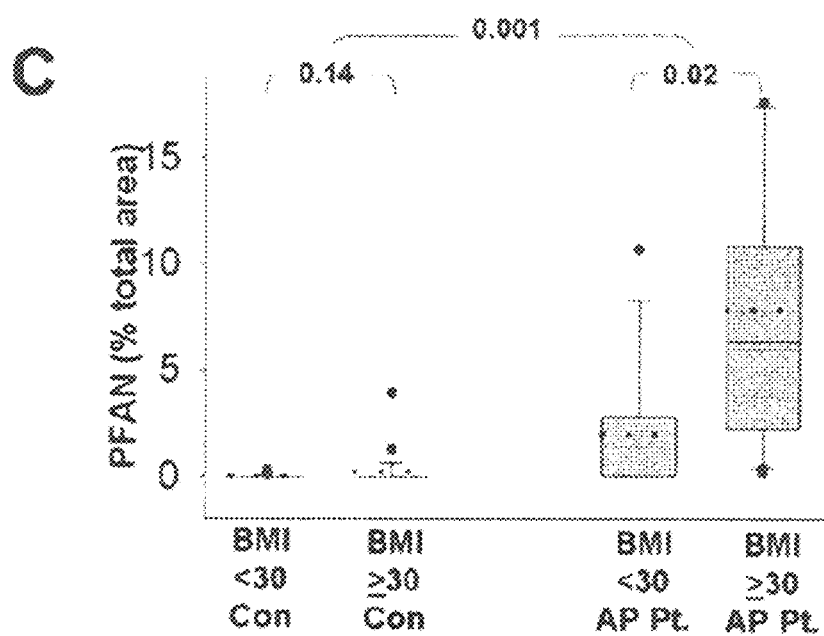

FIGURE 13A-C
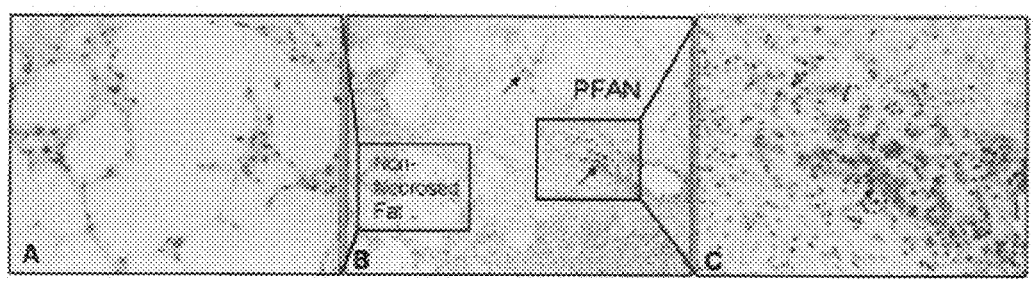

FIGURE 15A-B

FIGURE 17A-B

FIGURE 19A-B
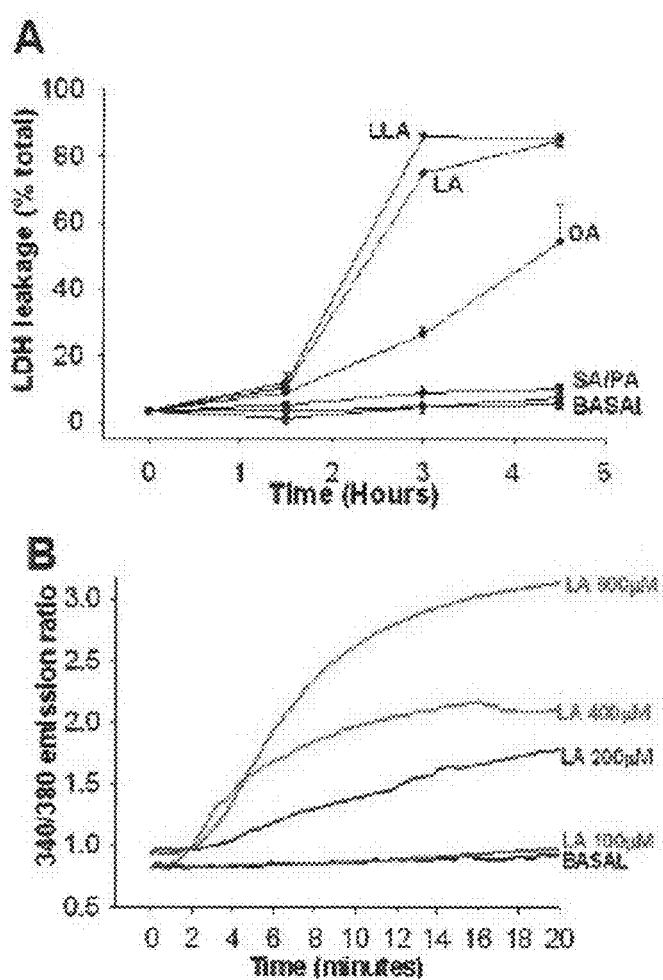

FIGURE 20A-B
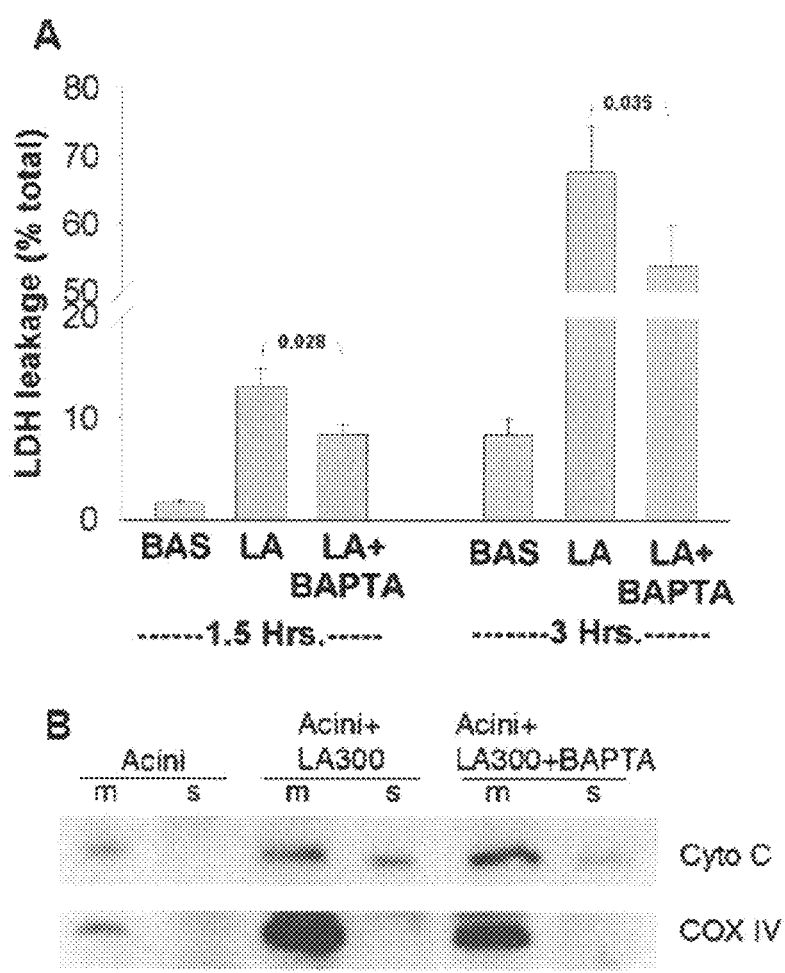

FIGURE 21A-C
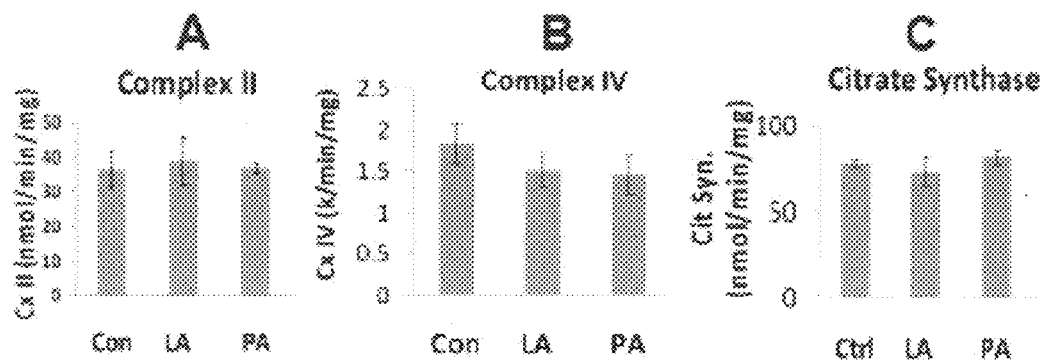

FIGURE 22A-E
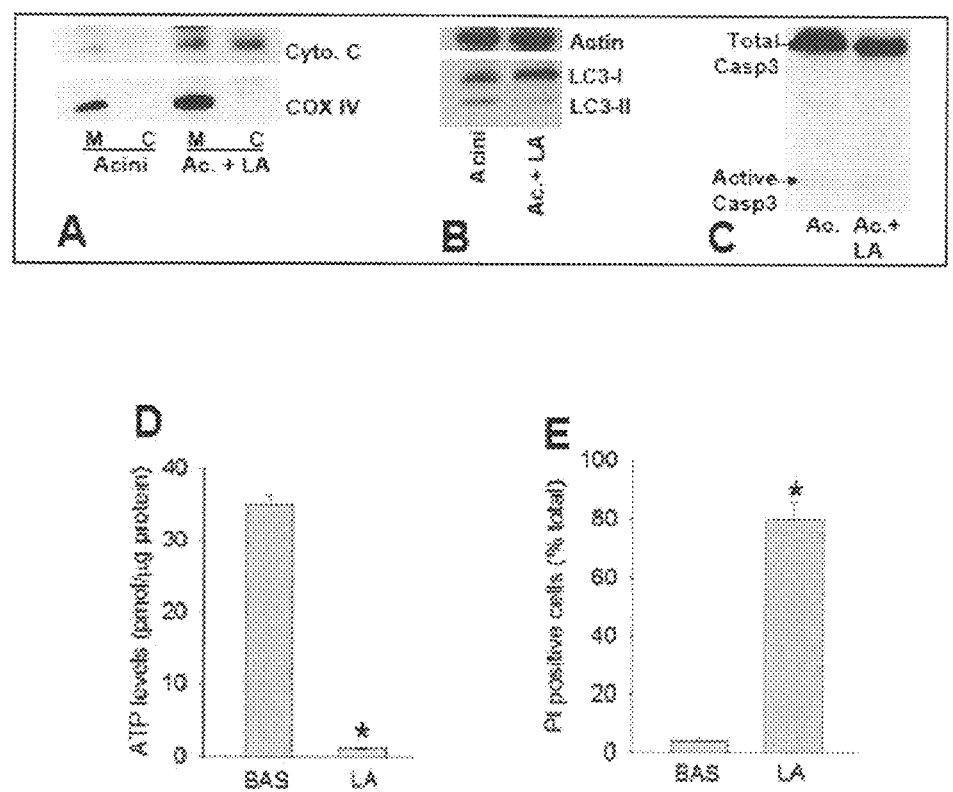

FIGURE 23A-B
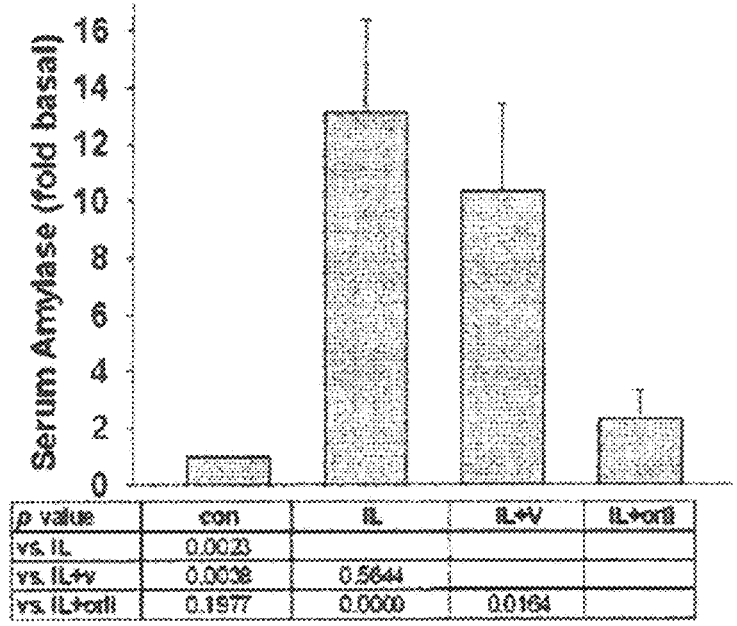
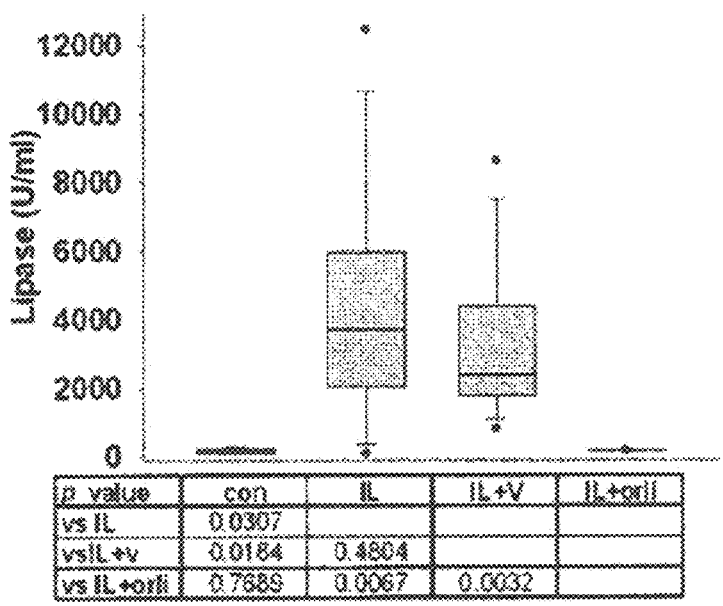

FIGURE 25A-F
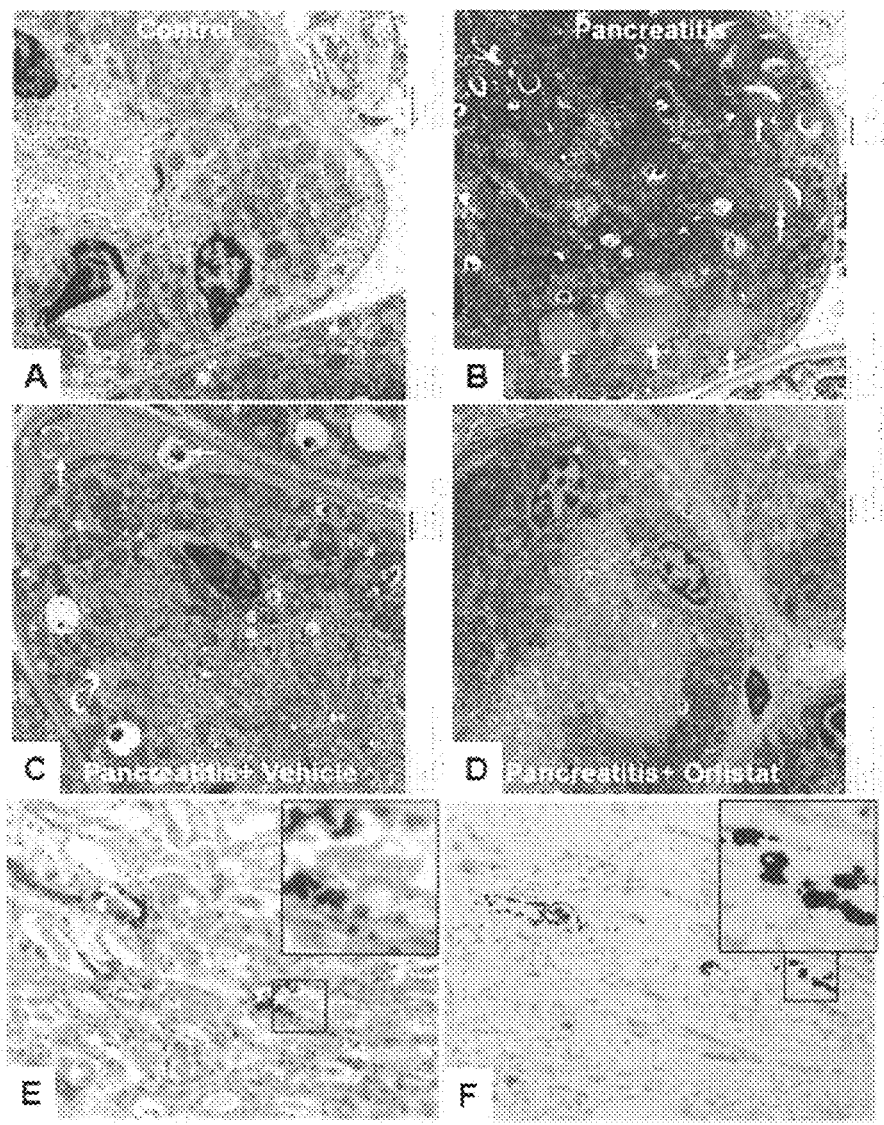

FIGURE 26A-D
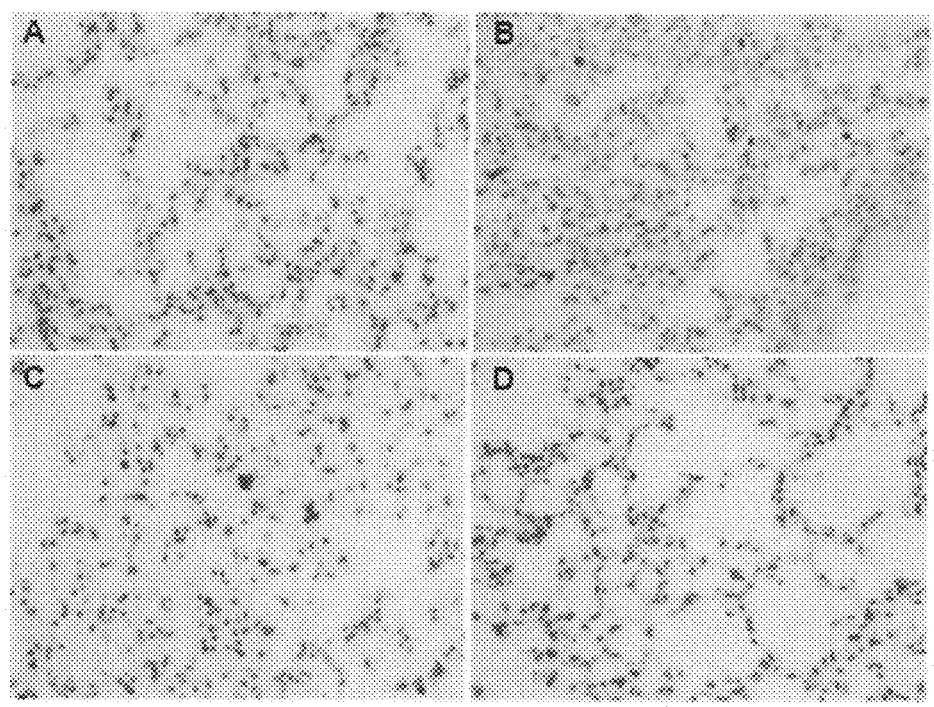

FIGURE 27A-C
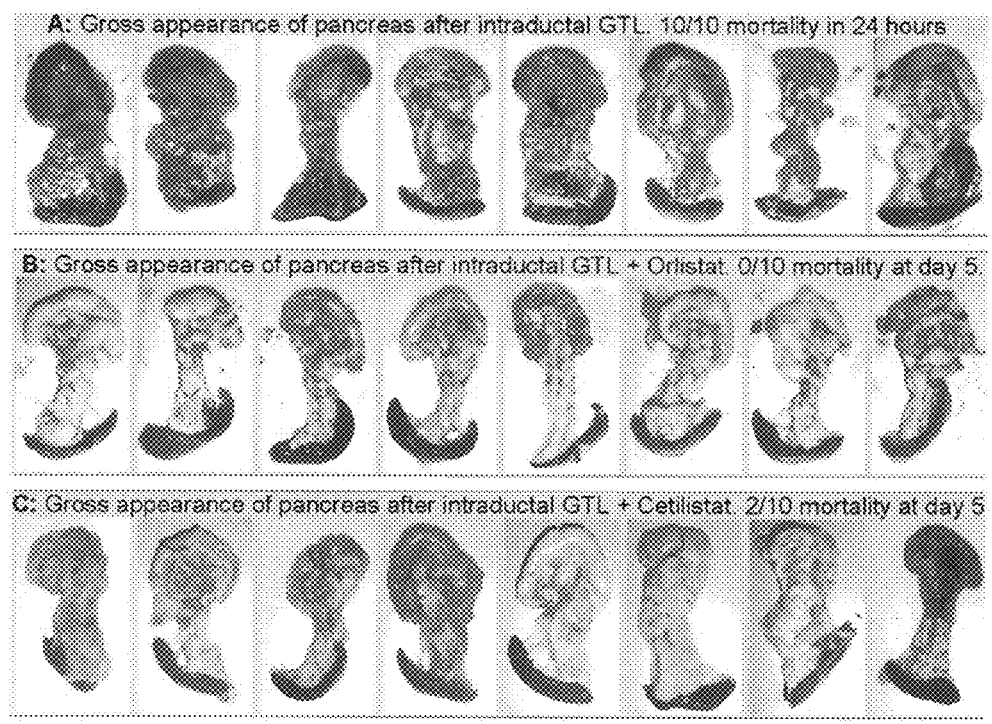

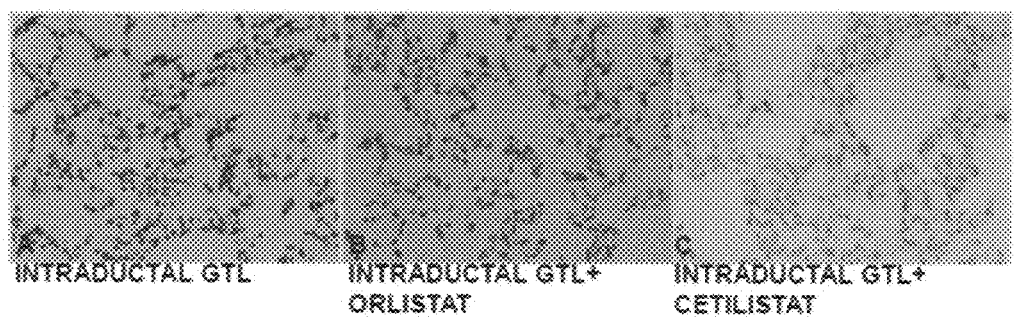
FIGURE 28A-C

FIGURE 29A-C
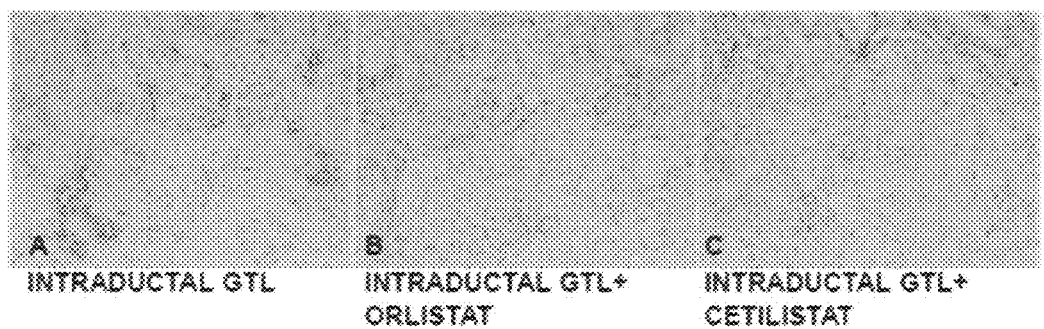

US 9,943,499 B2

LIPASE INHIBITORS FOR THE TREATMENT OF PANCREATITIS AND ORGAN FAILURE

PRIORITY CLAIM

This application is a divisional of U.S. patent application Ser. No. 13/447,850, filed on Apr. 16, 2012, and claims priority to U.S. Provisional Application No. 61/476,119, filed on Apr. 15, 2011, the contents of which are hereby incorporated by reference in their entireties herein.

GRANT INFORMATION

This invention was made with government support under Grant Number UL 1 RR024153 from the National Center for Research Resources, a component of the National Institutes of Health and DK092460 from the National Institutes of Health. The government has certain rights in the invention.

1. INTRODUCTION

The present invention relates to the use of lipase inhibitors for the treatment of pancreatitis and/or organ failure.

2. BACKGROUND OF THE INVENTION

Obesity is a well documented risk factor for worse outcomes in acute pancreatitis (Martinez, et al., Pancreatology 2006, 6:206-209; Papachristou, et al., Pancreatology 2006, 6:279-285; Sempere, et al., Pancreatology 2008, 8:257-264; Karimgani, et al., Gastroenterology 1992, 103: 1636-1640), including the risk of local complications (Tsai C J, Dig Dis Sci 1998, 43:2251-2254; Funnell, et al., Br J Surg 1993, 80:484-486), systemic complications such as the systemic inflammatory response syndrome (SIRS), multisystem organ failure (MSOF) and mortality (Papachristou, et al., Pancreatology 2006, 6:279-285; Karimgani, et al., Gastroenterology 1992, 103:1636-1640; Funnell, et al., Br J Surg 1993, 80:484-486; Johnson, et al., Pancreatology 2004, 4:1-6) and the risk of local complications. The sites of visceral fat deposition include the mesentery, omentum, liver (Park, et al., J Gastroenterol Hepatol 2008, 23:900-907), the pancreas, and the peripancreatic space (Olsen T S, Acta Pathol Microbiol Scand A 1978, 86A:367-373; Rosso, et al., J Gastrointest Surg 2009, 13:1845-1851; Saisho, et al., Clin Anat 2007, 20:933-942; Schmitz, et al., Pathol Res Pract 1981, 173:45-53). It has been suggested that visceral adipose tissue, as measured by waist-to-hip ratio and waist circumference above ideal cut-off value, may be a greater risk factor for worse outcomes in acute pancreatitis than total body fat (Mery, et al., Pancreatology 2002, 2:543-549; Martinez, et al., Pancreas 1999, 19:15-20). Mechanisms of this may include an elevated baseline proinflammatory state (Ghanim, et al, Circulation 2004, 110:1564-1571) and an exaggerated inflammatory response (Sempere, et al., Pancreatology 2008, 8:257-264) associated with obesity. Levels of proinflammatory cytokines such as Interleukin-1β and tumor necrosis factor-α are increased in pancreata of obese mice (Mathur, et al., Nonalcoholic fatty pancreas disease, HPB (Oxford) 2007, 9:312-318). Increased fat accumulation in the pancreas and peripancreatic space has been noted in association with increased body weight (Olsen T S, Acta Pathol Microbiol Scand A 1978, 86A:367-373; Saisho, et al., Clin Anat 2007, 20:933-942; Schmitz, et al., Pathol Res Pract 1981, 173:45-53).

Intrapancreatic fat has been shown to increase with BMI in studies evaluating autopsy samples (Olsen T S, Acta Pathol Microbiol Scand A 1978, 86A:367-373; Saisho, et al., Clin Anat 2007, 20:933-942; Schmitz, et al., Pathol Res Pract 1981, 173:45-53) surgically resected samples (Rosso, et al., J Gastrointest Surg 2009, 13:1845-1851) and radiological appearance of the pancreas (Saisho, et al., Clin Anat 2007, 20:933-942; Matsumoto, et al., Radiology 1995, 194: 453-458). The distribution of fat is fairly uniform in the dorsal pancreas and is reduced in the ventral pancreas (Schmitz, et al., Pathol Res Pract 1981, 173:45-53). Uneven fatty replacement in the pancreas is infrequent (3.2%), and the pattern of fat distribution is not influenced by obesity (Matsumoto, et al., Radiology 1995, 194:453-458).

The pancreas produces enzymes that aid in digestion and absorption of food; one such enzyme is lipase, which digests fat. A number of inhibitors of pancreatic lipase, which can inhibit absorption of ingested fat and thereby reduce caloric intake, have been developed as anti-obesity drugs. Examples of pancreatic lipase inhibitors include orlistat (marketed as the prescription drug Xenical by Roche and as an over-the-counter drug, Alli, by GlaxoSmithKline), cetilistat, and lipstatin. Orlistat has been reported to promote apoptosis and reduce cell grown and lymph node metastasis in a mouse melanoma model (Carvalho et al., Int. J. Cancer 2008, 123:2557-2565).

3. SUMMARY OF THE INVENTION

The present invention relates to methods and compositions for treating pancreatitis and/or organ failure comprising administering, to a subject in need of such treatment, an effective amount of a lipase inhibitor. It is based, at least in part, on the discoveries that lipotoxicity contributes to inflammation, multisystem organ failure, necrotic pancreatic acinar cell death and in acute pancreatitis, and that inhibition of lipolysis was able to reduce indices associated with these conditions. Accordingly, in various embodiments, the present invention provides for methods and compositions for limiting lipotoxicity and thereby reducing the likelihood of poor outcomes associated with acute pancreatitis and other severe systemic conditions, especially in obese individuals. In certain non-limiting embodiments, the invention provides for an improved formulation of lipase inhibitor combined with solubility enhancing agents.

4. BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1A-C. Representative images of pancreatic sections showing amount of intrapancreatic fat as quantified by the pathologist. (A) No fat (0%). The section shows pancreatic tissue with rare adipocytes (less than 0.5% fat). This was quantified as 0%. (A') shows a magnification of the area outlined by the box in A. (B): Section showing 10% intrapancreatic fat. (B') shows the area outlined by the box in B. Note this is composed of interlobular adipose tissue. (C) Section showing 70% intrapancreatic fat. Note the area of fat is bounded by 2 areas of pancreatic tissue and thus was included as intrapancreatic fat. (C') shows a magnification of the boxed area highlighting the presence of adipose tissue.

Figure 2:
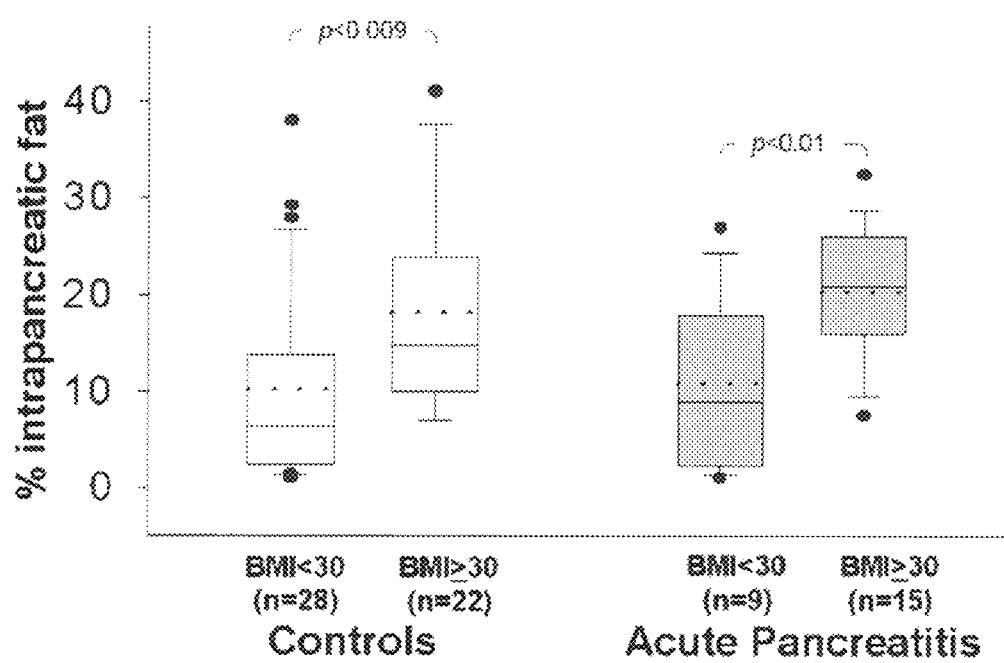

FIG. 2. Obese individuals have a higher percentage of intrapancreatic fat irrespective of acute pancreatitis. Graph showing box plots of the % intrapancreatic fat in lean and overweight (BMI<30) and obese (BMI>30) control patients (white boxes, left set) and patients with an autopsy diagnosis of acute pancreatitis (grey boxes, right set). The numbers in parenthesis denote number of patients in each group. The dotted line depicts the mean. The p value depicts the significance of difference between the two groups.

Figure 3:
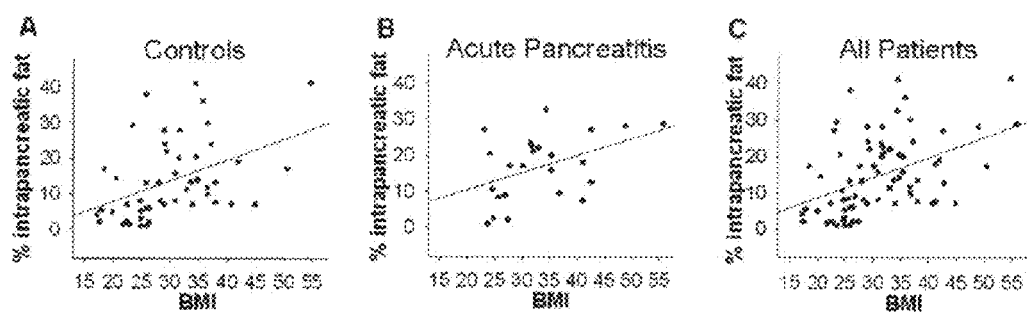

FIG. 3A-C. Intrapancreatic fat increases with BMI in both controls and acute pancreatitis patients. Correlation analysis between BMI and percent intrapancreatic fat. Each dot represents the value for an individual patient. (A) Relation in controls r=0.431,p=0.002 (B) Relation in acute pancreatitis patients p r=0.446,p<0.03 (C) Relation in both controls and acute pancreatitis combined, r=0.445, p<0.001

Figure 4:
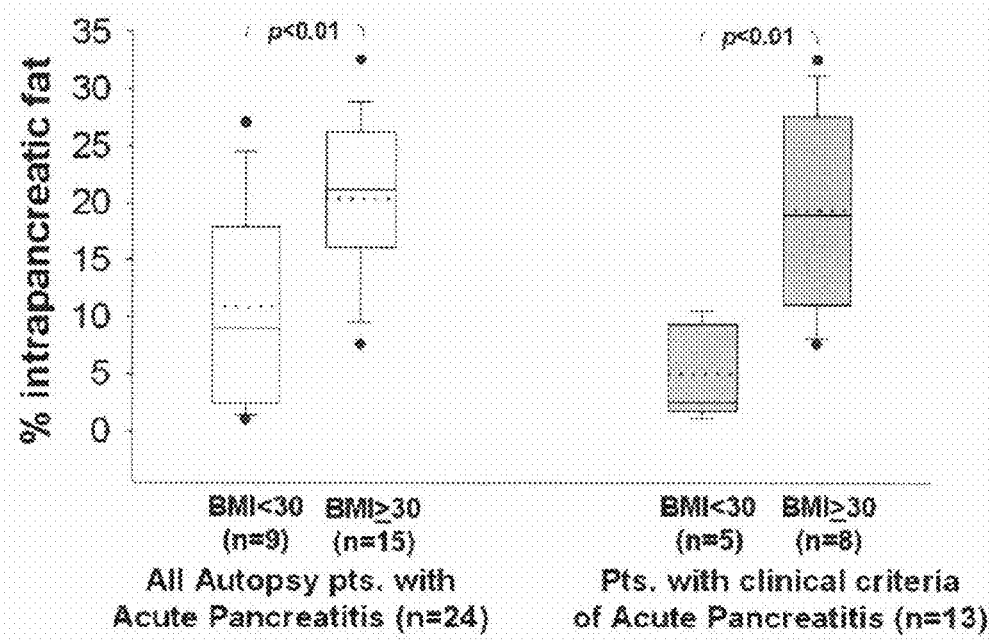

FIG. 4. Obese patients with acute pancreatitis have similar intrapancreatic fat percentage irrespective of whether it is an autopsy diagnosis or a clinical diagnosis: Comparison of intrapancreatic fat percentage in lean and obese patients with an autopsy diagnosis of acute pancreatitis (left set, in white) and those with a clinical diagnosis of acute pancreatitis (right set, in grey). The numbers in parenthesis denote number of patients in each group. The dotted line depicts the mean. As can be seen, obese patients had significantly higher (p<0.01) amounts of intrapancreatic fat in both sets.

FIG. 5A-B. Patients with clinically severe acute pancreatitis have higher BMIs and intrapancreatic fat. (A) Box plots showing a comparison of BMIs of patients with clinically mild (left) and severe (right) acute pancreatitis. The BMIs of patients with severe acute pancreatitis were significantly higher (p<0.03) than those with mild acute pancreatitis. (B) Box plots showing a comparison of percent intrapancreatic fat of patients with clinically mild (left) and severe (right) acute pancreatitis. The intrapancreatic fat percentage of patients with severe acute pancreatitis were significantly higher (p<0.003) than those with mild acute pancreatitis. The numbers in parenthesis denote number of patients in each group. The dotted line depicts the mean.

FIG. 6A-G. BMI Increases IPF with high UFAs worsening pancreatic injury: (A) % IPF in controls (white), AP on autopsy (light grey), clinical AP (dark grey) patients with BMI <30 or BMI ≥(first 3 pairs), clinically mild and severe AP (fourth pair) patients. (B) Non contrast CT (thresholding method) vs. histology % IPF correlation. Human pancreatitis serial sections stained for calcium (C), H&E (C') showing fat necrosis (quadrangle), parenchymal injury (dotted polygon) around calcium staining (dashed ovals). Acinar necrosis (D), fat necrosis (E) PFAN box plots (F) in controls, mild (mild) and severe AP. (G) % NEFAs in human pancreatic necrosis debridement fluid, White, black bars respectively show UFAs and SFAs. Table 1 shows p values.

FIG. 7A-G. Lipolysis of adipocyte triglyceride causes acinar cell necrosis. Propidium Iodide (PI) uptake in control acini (A), co-cultured without (B), m with 50 μM orlistat (Ac+orli), with adipocytes with (Ac.+Ad) or with 50 μM orlistat (Ac+Ad+orli). (F) Cytochrome C (Cyto. C, upper panel) in mitochondrial (M), cytoplasmic (C) fractions of Acini alone, co-cultured without (ac+Ad.) and with 50 μM orlistat (Ac.+Ad.+Orli). Lower panel: Mitochondrial marker COX IV. (G) NEFA concentration in medium of Acini, adipocytes (Adipo.), co-culture without (Acini+Adipo.) or with 50 μM orlistat (Acini+Adipo+Orli).

FIG. 8A-H. UFAs induce acinar necrosis and inflammatory mediator generation: (A) Intra-acinar calcium increase (Cai) with 600 μM fatty acids (LLA: linolenic, LA; Linoleic, OA, Oleic, SA: Stearic, PA; palmitic acid). (B) 1 μM thapsigargin (Thaps.) but not EGTA (1 mM) prevents 600 μM LA induced Cai increase (C) Acinar LDH leakage at 5 hours. Complex 1 (D), V(E) activity in control acini (CON), with 300 μM LA or 1200 μM PA. Bar graphs with SEM showing TNF-α (F), CXCLI (G), and CXCL2 (H) mRNAs induced by 200 μM LA, 200 μM PA compared to controls (Con.).

FIG. 9A-G. Lipolysis worsens pancreatic damage in obese mice: (A, A') Calcium (A), H&E (A') stained serial sections showing pancreatic fat necrosis (black, brown in A, blue in A'), surrounding parenchymal injury (pink, blue areas with loss of cellular detail in A, A' respectively). Dotted area in A; saponified parenchymal fat. Gross images in vehicle (B,C) or orlistat treated animals with pancreatitis (B', C'), peritoneal cavity (C, C'). Note orlistat prevents saponification. Serum calcium (D), pancreatic necrosis (E), fat necrosis (F) PFAN (G) (as % of total area), in controls (Con), pancreatitis (IL), vehicle (IL+Veh), orlistat (IL+Orli) treatment. Shown below are p values.

FIG. 10A-M. End-organ damage and mortality in obese mice are prevented by inhibiting lipolysis: (A) % NEFAs in Adipose tissue triglyceride of lean (white bars), obese mice (black bars). (B). Serum UFAs (micromoles/liter) in controls (Con), pancreatitis (IL), vehicle (Veh), pancreatitis with vehicle (IL+Veh), orlistat treatment (IL+Olri). (C) Table showing mortality in ob/ob mice Kidney H&E (D-D3), Oil-red-O staining (60×) (E-E3), TUNELS (F-F3) in controls (E, F, J), Pancreatitis (E1, F1, J1), pancreatitis with vehicle (E2, F2, J2), pancreatitis with orlistat treatment (E3, F3, J3). BUN (G), lung section apoptotic count (H), Lung MPO (I), serum adipokines, cytokines (J, K, L., M). Shown below are p values.

FIG. 11A-B. Quantification of IPF by CT method 1 and its correlation with histology. (A) shows representative images of pancreatic attenuation measurement by placing a total of 9 circular regions of interests (ROIs; 1 cm in maximum diameter) over the head (n=3), body (n=3), and tail (n=3) of the pancreas and quantifying these as Hounsfield units (HU). (B) shows the correlation of the mean pancreatic attenuation (as HUs) with the % IPF on CT scanning for each patient.

FIG. 12A-C. Box plots comparing acinar necrosis (A), fat necrosis (B) and peri-fat acinar necrosis (PFAN) (C) among non-obese non-obese (BMI<30, and obese (BMI≥30) controls and acute pancreatitis patients (AP Pt.), shown as a percentage of total area. The p value comparing the various groups is shown above each graph. The dotted line depicts the mean.

FIG. 13A-C. CD68-positive macrophages accumulate around areas of peri-fat acinar necrosis. Immunostaining for CD68 shows weak positivity in or around non-necrosed fat (A, inset of B). However, this dramatically increased in areas surrounding fat-necrosis and peri-fat acinar necrosis (PFAN, inset of B and C; arrows point toward CD68-positive cells).

Figure 14:
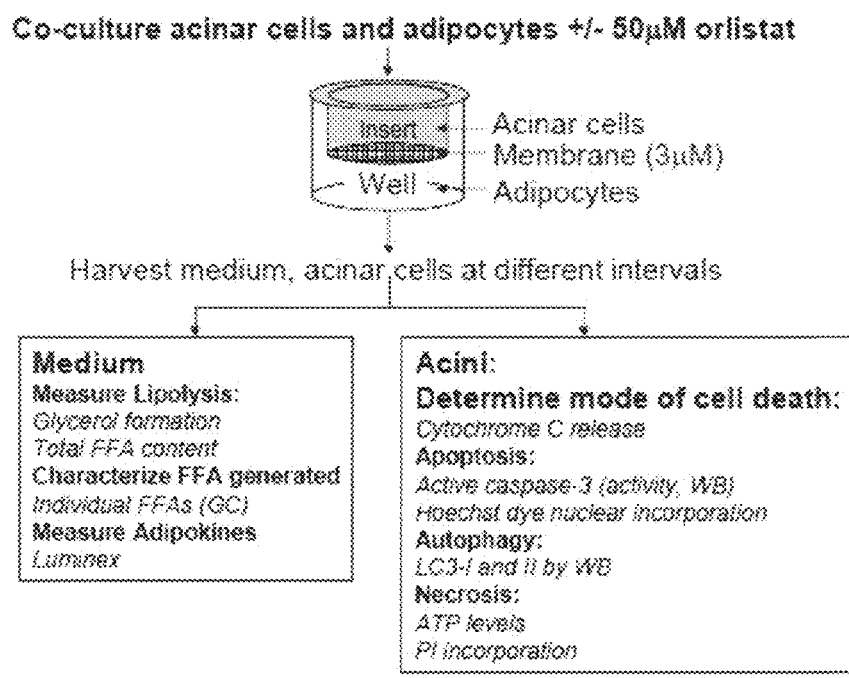

FIG. 14. Schematic showing the setup of the co-culture system and sources used for assays.

FIG. 15A-B. (A): Acinar autophagy is not induced in the co-culture, as evidenced by lack of increase of lipidated form of LC3 (LC3-II) over control levels whether acini (Ac.) are cultured with adipocytes in the absence (Ac+Ad.) or in the presence of 50 μM orlistat (Ac+Ad+Orli). Chymotrypsin (Chymo.) was used as marker of acinar cells and perilipin (Perilip.) for adipocytes (Ad.). Each marker was present only in the appropriate homogenate signifying lack of contamination by other cell type. (B). There is no increase in active caspase 3 (casp3) over control acinar levels (Ac.) whether acini (Ac.) are cultured with adipocytes in the absence (Ac+Ad.) or in the presence of 50 μM orlistat (Ac+Ad+Orli), signifying no evidence of apoptosis.

Figure 16:
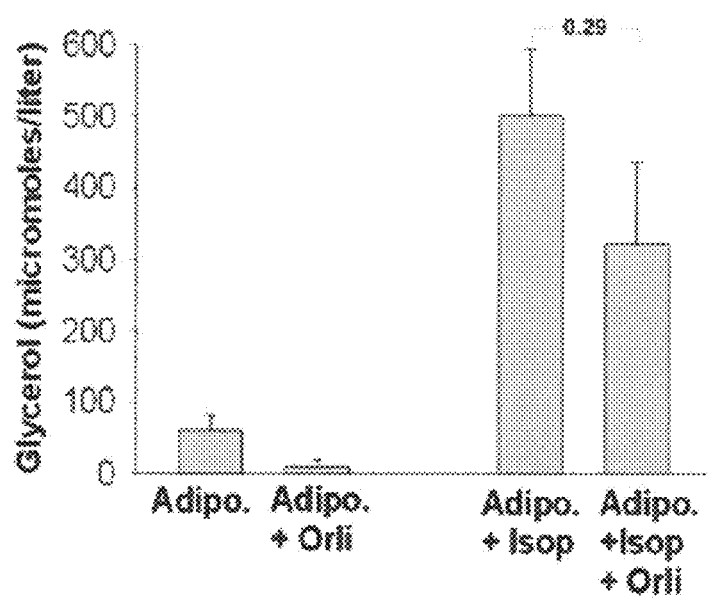

FIG. 16. Glycerol release, in the medium after 1 hour of adipocyte (Adipo.) culture. The 10 μM isoprotrenol (Isop)

stimulated increase in glycerol levels was not significantly prevented by 50 μM orlistat (Orli), supporting its role as a inhibitor of lipases and its low permeability through cell membranes.

FIG. 17A-B. (A) Trypan blue uptake in control acini and after co-culture with adipocytes without (acini+adipocytes) and with 50 μM orlistat (orli). Note the ubiquitous uptake in the absence of orlistat, signifying acinar injury. (B) Whereas acini co-cultured with adipocytes in the absence of orlistat (acini+Adipocytes) exhibit no secretory response under basal conditions (Bas), or in response to physiologic (100 pM) and supraphysiologic (100 nM) doses of caerulein, after co-culture with adipocytes in the presence of 50 μM orlistat (acini+Adipo+Orli), the acini exhibit an amylase secretory pattern like control acini incubated alone (Acini), signifying retained function. * and ** indicates significant ($p<0.05$) difference in values compared with basal and both basal and 100 pM caerulein respectively.

Figure 18:
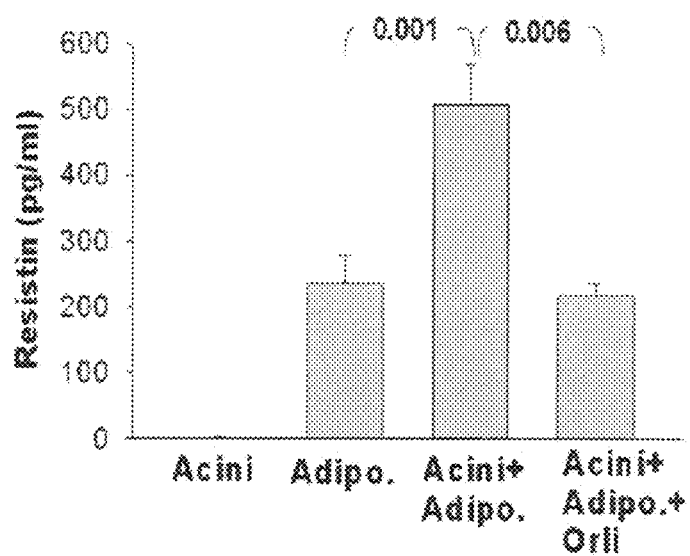

FIG. 18. Inhibition of lipolysis prevents increase in resistin. Resistin levels measured in the medium harvested after culturing acini alone (Acini), adipocytes alone (Adipo.), and co-culture with adipocytes in the absence (Acini+Adipo.) or in the presence of 50 μM orlistat (Acini+Adipo+Orli).

FIG. 19A-B. Time course of acinar LDH leakage (A) with 300 μM fatty acids (LLA; linolenic acid, LA; Linoleic acid, OA; Oleic acid, SA; Stearic acid, PA; palmitic acid). (B) Dose response of increase in intracellular calcium levels with different concentrations of linoleic acid added to acinar cells.

FIG. 20A-B. (A) Effect of 30 μM BAPTA on 300 μM linoleic acid (LA) induced LDH leakage at 90 minutes and 3 hours. The significant reduction by BAPTA at these time points could not be sustained over the 5 hours of the experiment. EGTA (1 mM) was ineffective in preventing LDH leakage at both the 90 minute (21.2±8.3%) or at the 3 hour time point (54.6±6.4%, p=0.41). (B) Cytochrome C (Cyto. C, upper panel) in mitochondrial pellet (M), and cytoplasmic supernatant (S) fractions of Acini alone (Acini), Acini after incubation with 300 μM linloeic acid (Acini+LA300) for 90 minutes and Acini preincubated with 30 μM BAPTA for 30 minutes flowed by addition of 300 μM linloeic for 90 minutes (Acini+LA300+BAPTA). The reduction in cytochrome C leakage into the cytoplasmic supernatant was not significantly reduced by BAPTA.

FIG. 21A-C. Complex II (A), IV (B) and citrate synthase (C) activities in control acini (CON) acini and those treated with 300 μM LA or 1200 μM. There was no significant difference induced by LA or PA compared with controls.

FIG. 22A-E. (A) Cytochrome C leakage from the mitochondrial fraction (M) to the cytosolic fraction (C) induced in acini (Ac.) by 300 μM linoleic acid (LA) at 1.5 hours. COX IV was used as mitochondrial loading control. Autophagy (B) and apoptosis (C) are not activated by 300 μM linoleic acid (LA) as shown by lack of increase in LC3-II and active caspase3, respectively. (D) Acinar ATP levels induced by 300 μM linoleic acid (LA) at 5 hours. E: Propidium iodide (PI) uptake induced by 300 μM Linoleic acid (LA) at 5 hours. * indicates a p=0.0000.

FIG. 23A-B. Serum amylase (A) and lipase (B) levels compared between controls (Con), pancreatitis (IL), pancreatitis+vehicle (IL+Veh), and pancreatitis+orlistat (IL+Orli). The p values between different groups are shown below the graphs. Note orlistat significantly reduced all of these compared with IL or IL+Veh groups.

Figure 24:
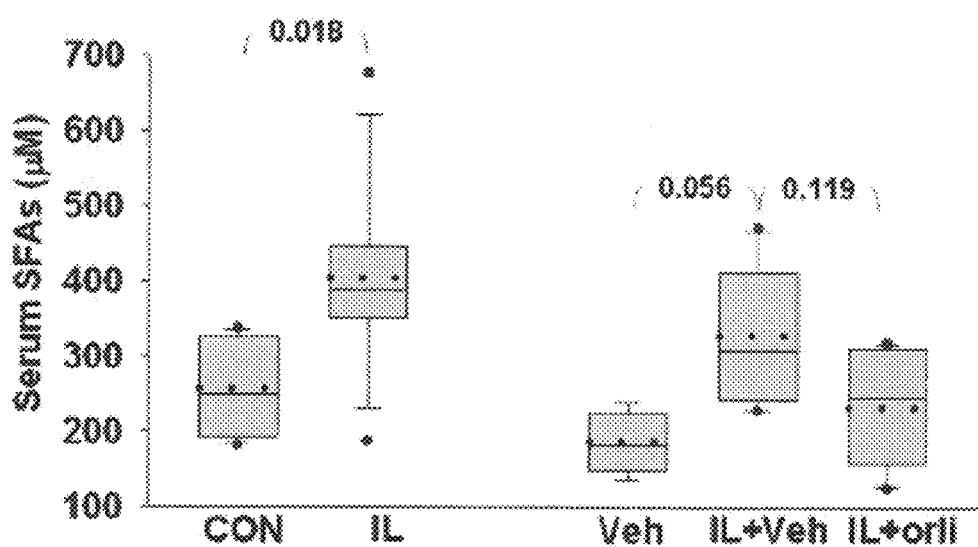

FIG. 24. Serum saturated fatty acid levels (SFA) in controls (Con), pancreatitis (IL), vehicle (Veh), pancreatitis+vehicle (IL+Veh), and pancreatitis +orlistat (IL+Orli). The p values between different groups are shown above. Orlistat (IL+Orli) did not significantly reduce the SFA levels compared with the IL+Veh group.

FIG. 25A-F. (A-D) Electron microscopy images from controls (Control, 4400×) (A), pancreatitis, 3400× (B), pancreatitis+vehicle, 3400× (C), and pancreatitis+orlistat, 3400× (D) treated mice showing lipid vacuoles, some of which have dense deposits of calcification (Arrows) and mitochondrial swelling. Orlistat reduces these in the animals with pancreatitis. (E, F) Human kidney serial sections from patient dying with acute renal failure resulting from acute pancreatitis showing tubular damage on hematoxylin and eosin (E) and calcification on Von Kossas (F).

FIG. 26A-D. Lung TUNELs (40×) in controls (A), ob/ob pancreatitis (B), pancreatitis with vehicle (C), and pancreatitis with orlistat treatment (D).

FIG. 27A-C. Gross pancreatic appearance at the time of necropsy after intraductal infusion of GTL (A), GTL+orlistat (B), GTL+cetilistat (C). Each image show individual pancreata with the head, duodenal loop in at the top and the pancreatic tail, with attached spleen at the bottom. Note the extensive hemorrhage and gross evidence of necrosis in panel A images. These are absent in panel B, and only present in the last image in panel C (animal died on day 1).

FIG. 28A-C. TUNEL staining of lung sections. (A) Lung section of a rat dying with GTL induced pancreatitis showing numerous brown staining TUNEL positive nuclei (arrows). (B): Lung section of a rat administered GTL with orlistat showing absence of TUNEL positive nuclei. (C): Lung section of a rat administered GTL with Cetilistat showing absence of TUNEL positive nuclei.

FIG. 29A-C. TUNEL staining of kidney sections. (A) kidney section of a rat dying with GTL induced pancreatitis showing numerous brown staining TUNEL positive nuclei in the tubules. (B) kidney section of a rat administered GTL with or (C) kidney section of a rat administered GTL with cetilistat showing absence of staining TUNEL positive nuclei.listat showing absence of staining TUNEL positive nuclei.

5. DETAILED DESCRIPTION OF THE INVENTION

The present invention relates to methods and compositions for treating pancreatitis comprising administering, to a subject in need of such treatment, an effective amount of a lipase inhibitor. Effective treatment of pancreatitis is indicated by, for example and not by way of limitation, a decrease in serum level of pancreatic enzyme(s), improved radiologic findings, and/or a decrease in secondary organ failure, hypocalcaemia and/or systemic inflammation.

Non-limiting embodiments of the invention provide for a method for treating acute pancreatitis in an obese subject comprising administering, to the subject, an effective amount of a pancreatic lipase inhibitor.

A subject may be a human subject or a nonhuman subject, such as, but not limited to, a dog, cat, horse, cattle, sheep, goat, or rodent.

Non-limiting embodiments of the invention provide for a method of reducing the risk of organ failure in a subject suffering from acute pancreatitis comprising administering, to the subject, an effective amount of a pancreatic lipase inhibitor. Organs for which the risk of organ failure may be reduced include the kidney (where failure is referred to as renal failure), the lung (where failure is referred to as pulmonary failure), as well as multisystem organ failure (e.g. multiple organ dysfunction syndrome involving at least these two organs). The status of these organs may be determined using clinical methods well known in the art. For example, and not by way of limitation, kidney function (and the development of renal failure) may be assessed via increased blood urea nitrogen levels, increased creatinine, decreased urine output, and/or histologic findings; lung function and the development of pulmonary failure may be assessed using pulmonary function tests, blood gases (oxygen and carbon dioxide levels), oxygen supplementation requirements (e.g. nasal cannula or face mask or ventilator, with different percentages and flow rates of oxygen) and/or histologic findings; (for indices of organ failure, see J. Wallach, 1978, *Interpretation of Diagnostic Tests*, Third Edition, Little, Brown and Co., Boston, and/or J. Wallach, 2006, *Interpretation of Diagnostic Tests*, Eighth Edition, Lippincott Williams & Wilkins, both incorporated by reference in their entireties). Likewise, an index of systemic inflammation is an increase in levels of one or more inflammatory mediators, including but not limited to tumor necrosis factor alpha, monocyte chemotactic protein 1 and/or interleukin 6. These embodiments are supported, at least in part, by working examples below, which show the effectiveness of pancreatic lipase inhibitors in decreasing the risk of multisystem organ failure.

In certain non-limiting embodiments of the invention, a pancreatic lipase inhibitor may be administered to the subject intraperitoneally, intravenously, orally, via a sustained release implant, subcutaneously, intramuscularly, or by another route known in the art.

The term "obese" as used herein refers to a subject having a body mass index of greater than 25 and particularly greater than or equal to 30.

Non-limiting embodiments of the invention provide for a method for treating acute pancreatitis in an obese subject comprising administering, to the subject, an effective amount of a pancreatic lipase inhibitor. In certain non-limiting embodiments, such administration may be achieved, for example, in the region of the pancreas of the subject, by administering the lipase inhibitor intraperitoneally, for example as a solution or a sustained-release implant, or by another route.

In non-limiting embodiments of the invention, the pancreatic lipase inhibitor is orlistat or cetilistat. According to certain embodiments of the invention orlistat or cetilistat is administered non-orally, for example by local injection or administration to the region of the pancreas, for example by intraperitoneal infusion. In certain embodiments orlistat or cetilistat may be administered in an alcohol solution. For example, but not by limitation, where the subject is a human the daily dose may be between 1 and 50 mg/kg or between 5 and 20 mg/kg, or between 7 and 15 mg/kg or between 3 and 12 mg/kg, or between 10 and 15 mg/kg, or between 1 and 5 mg/kg, or about 10 mg/kg, which may be administered as a single dose or as a divided dose (e.g., twice a day (BID), three times a day (TID) or four times a day (QID)). For example, and not by way of limitation, the daily dose may be administered in a dosage regimen for 1, 2, 3, 4, 5, 6, 7, 8, 9, 10, 11, 12, 13, 14, 15, 16, 17, 18, 19, or 20 days. For example, and not by way of limitation, the daily dose may be administered every day, or every other day, or every third day, or every fourth day, or every fifth day, or every sixth day, or once a week. A dosage regimen may be repeated as clinically required. A dosage may be administered together with food or other means of enteral or parenteral nutrition.

Alternative pancreatic lipase inhibitors that may be used according to the invention include, but are not limited to, lipstatin, panclicins A, B, C, D, or E, CT-II (from an extract of Nomame herba; Yamamoto et al., 2000, Int. J. Obesity 24(6):758-764), and 3-0-tran-p-coumaroyl actinic acid. For example, the dose of an alternative pancreatic lipase inhibitor may be determined based on the orlistat and cetilistat doses set forth herein by adjusting the dose based on the relative inhibitor potency of the compounds.

In certain non-limiting embodiments, the invention provides for an improved formulation of lipase inhibitor combined with solubility enhancing agents. The lipase inhibitor may be, for example, and not by limitation, orlistat, cetilistat, or a combination thereof or a derivative of either. Solubility enhancing agents comprise one or more triglyceride form of a fatty acid and one or more bile salt. Suitable fatty acids (to be used in triglyceride form) include but are not limited to oleic, linolenic, palmitic, stearic or short chain fatty acids and combinations thereof (for example, a triglyceride where not all the fatty acids linked are the same; mixtures of triglycerides where all fatty acids linked to a triglyceride are the same; and mixtures where some triglycerides comprise the same fatty acid and other triglycerides comprise more than one species of fatty acid). Suitable bile salts include, but are not limited to, taurocholate, or taurochenodeoxycholic acid ( taurochenodeoxycholate), taurolitholcholic acids (taurolithocholate), or bile acids like cholic acids, lithocholic acid or their glycine conjugates and/or sodium salts thereof, and combinations thereof. The amount of bile acid administered is sufficient to enhance solubility but insufficient to produce substantial toxic effect. In certain non-limiting embodiments, the amount of bile acid administered, when distributed in the total body volume of the subject, approximates physiologic levels, for example, but not limited to, is between 0.01 and 10 fold body levels. In certain embodiments of the invention, a formulation comprises a lipase inhibitor and solubility-enhancing amounts of a triglyceride form of one or more fatty acids and a bile salt. In certain embodiments, said formulation may be prepared by preparing a first solution comprising a lipase inhibitor and a solubility-enhancing amount of a triglyceride form of one or more fatty acid, with optional gentle warming (for example, heating to between about 30-50 degrees Centigrade or to between 35 and 40 degrees Centigrade or to about 40 degrees Centigrade) and then adding a second solution comprising a solubility-enhancing amount of a bile salt, followed by mixing, for example, but not limited to, by sonication. In a specific, non-limiting embodiment, the solution can be prepared as follows: 75 mg of orlistat is weighed to which 187 microliters of glyceryl trilinoleate (GTL) is added, and the mixture is gently heated to for 15-30 seconds, with gentle shaking till clear. 3.75 mgs of sodium taurocholate is dissolved in 7.2 ml saline (phosphate buffered, with a pH of 7.4) in a separate container. The sodium taurocholate solution is added gradually in small (about 1 ml) aliquots to the orlistat GTL solution, and sonicated after the addition of one or each of these to produce a white solution.

6. EXAMPLE

Increased Intrapancreatic Fat is Associated with Obesity and Severe Acute Pancreatitis

6.1 Materials and Methods

We searched the University of Pittsburgh Medical Center—Presbyterian Hospital autopsy database from 1998 till 2008 and identified all patients who received a postmortem diagnosis of acute pancreatitis. The diagnosis of acute pancreatitis in all cases was based on gross and microscopic appearance at the time of autopsy. Of the 46 acute pancreatitis patients identified and had pancreas slides available for review, we excluded the 19 patients in whom the autopsy report also mentioned a pathologic diagnosis of chronic pancreatitis and two patients who were post Whipple resection for pancreatic cancer to avoid the changes that would occur secondary to these pathologies. An additional patient with acute pancreatitis whose slides showed severe hemorrhage and excessive autolysis was excluded since this would have precluded an accurate measurement of amount of fat.

Thus, the total sample size for acute pancreatitis patients was 24. From the remaining patients in the autopsy database, we randomly chose 50 subjects as controls for this study.

The slides of all patients and controls were retrieved and reviewed. The study was approved by the Committee for Oversight of Research Involving the Dead at the University Of Pittsburgh Medical Center. The electronic clinical records of patients with an autopsy diagnosis of acute pancreatitis were reviewed to assess whether a subject had clinical criteria for acute pancreatitis (serum amylase or lipase ≥3 fold upper limit of normal, typical abdominal pain or radiologic findings to support the diagnosis), and to assess the severity acute pancreatitis (defined as presence of single or multisystem organ failure attributable to acute pancreatitis, a mention of necrotizing pancreatitis on computed tomography report, or "widespread", "extensive" or "diffuse" necrosis noted at the time of autopsy). Of the 24 patients, thirteen met the clinical criteria for acute pancreatitis. All 13 had a ≥3 fold increase in amylase and/or lipase documented within the week before death. Of these 1 patient had all 3 criteria (pain, abnormal CT, increased enzymes), 7 patients had 2 criteria (abdominal pain and increased enzymes in 3 patients, and CT abnormalities with increased enzymes in 4 patients), 1 had a clinical diagnosis of acute pancreatitis listed on his hospitalization records, 3 were sedated/comatose on ventilator support when elevated pancreatic enzymes (>3fold increase in amylase/lipase) were documented (last week before death), and in one patient acute pancreatitis was suspected based solely on elevated pancreatic enzymes—this patient also had hypercalcemia during hospital admission. Of the 13 patients, five had severe acute pancreatitis based on—local complications ("extensive necrosis" or "severe necrotizing pancreatitis", "pancreatic hypo perfusion" mentioned on CT scan—3 patients or "diffuse" or "extensive" necrosis noted at the time of autopsy—all 5 patients). Four of these five patients had systemic complications of MSOF or acute respiratory distress syndrome attributed to acute pancreatitis.

The remaining 11 patients did not fulfill the clinical criteria for acute pancreatitis. Nine of these did not have serum amylase or lipase estimation in the 2 weeks prior to death. One patient had a 2 fold elevation three days before death (patient had history of alcohol abuse and cirrhosis) and 1 had normal enzymes 5 days before death. CT abdomen was done in only one of these 11 patients 9 days before death and was normal. Eight of the patients were on ventilator support 5 or more days before death. Of the remaining 3 patients, one had a history of alcohol abuse as described above, one had septic shock and was on the ventilator for 3 days prior to death (autopsy revealed focal fat necrosis and moderate congestion), and one died of cardiogenic shock in a background of systemic lupus erythematosus (autopsy revealed mild acute pancreatitis). In none of these was pancreatitis thought to be an immediate cause of death. In one of the 11 patients, acute pancreatitis was reported as an underlying cause of death. This patient was status post kidney pancreas transplant, was on a ventilator for 20 days and had pulmonary embolism as the immediate cause of death.

For histologic evaluation, we retrieved all hematoxylin and eosin stained slides of the pancreas (1-4 in number) of control and acute pancreatitis patients. A trained pathologist with specific interest in gastrointestinal pathology blinded to demographic and clinical data examined all slides to quantify intrapancreatic fat. Adipose tissue with large vessels and nerves not bounded by at least two pieces of pancreatic parenchyma was regarded as peripancreatic and excluded. The remaining adipose tissue was measured as a percentage area of each individual field. Examples demonstrating various amounts of intrapancreatic fat in a field are shown in FIG. 1A-F. The percentage of intrapancreatic fat for each individual field was added. The final number was divided by the number of fields to give a percentage intrapancreatic fat for that section. For patients with more than 1 section, the average of the percentage of intrapancreatic fat for all fields from different sections was chosen as representative for the specimen.

Statistical Analysis:

Continuous data is presented as mean±standard deviation (SD) and categorical data as proportions. Bivariate comparisons for continuous data were performed using the Student's t-test or Pearson correlation coefficient, and categorical data was compared using the chi-squared test or Fischer's exact test as applicable. Subjects with a BMI of <30 were classified as normal/overweight while those with a BMI of ≥30 were classified as obese. We used linear regression analyses to determine the factors predicting \intrapancreatic fat percentage. In these analyses, we used age (years), BMI (as continuous variable), disease status (control or acute pancreatitis case) as independent variables. No collinearity was detected on data analysis. A two-tailed p-value of <0.05 was considered as significant. The data was analyzed using SPSS version 17 software, Chicago, Ill.

6.2 Results

Obesity is associated with increased intrapancreatic fat in controls: We initially confirmed the findings published in previous studies showing a positive association between obesity and intrapancreatic fat 10-13. The mean age for controls was 64.2+16.0 years. While 22/50 (44%) of the controls were obese (mean BMI 37.4+6.1), the remaining 56% were normal or overweight (mean BMI 24.3+3.7). A significant correlation of intrapancreatic fat was seen with BMI (r=0.431,p=0.002, FIG. 3A) but not with age (r −0.063, p=0.662). The percentage intrapancreatic fat in obese controls was significantly higher compared to controls who were normal or overweight (18.3+10.8% vs. 10.3+9.9%; p<0.009) (FIG. 2, white boxes).

Obesity is associated with increased intrapancreatic fat in acute pancreatitis: Nine of the 24 patients (38%) with a diagnosis of acute pancreatitis were normal or overweight (BMI 25.3+1.7) and 15 (62%) were obese (BMI 38.2+7.2). The BMI in respective patient groups with acute pancreatitis was not significantly different from those of the corresponding control groups (p=0.62 and p=0.75 respectively). Similar to controls, a significant correlation for intrapancreatic fat percentage was seen with BMI (r=0.445,p<0.03, FIG. 3B) but not with age (r 0.088, p=0.681) and obese acute pancreatitis patients had significantly higher percentage of intrapancreatic fat than normal or overweight patients (20.8+7.1% vs. 10.9+9.0%,p<0.01, FIG. 2 grey boxes).

Intrapancreatic fat is similar in controls and acute pancreatitis patients irrespective of autopsy or clinical diagnosis: There was no significant difference between controls and acute pancreatitis cases for age, BMI (overall) and intrapancreatic fat percentage. The correlation between BMI and percent intrapancreatic fat is shown in FIG. 3A-B. The intrapancreatic fat percentage was not significantly different in acute pancreatitis patients from the amounts in their respective control groups (p=0.81 and 0.75 for normal or overweight patients and obese patients respectively). The intrapancreatic fat in patients with clinical acute pancreatitis was similar to those who only had a pathologic diagnosis of acute pancreatitis. This was noted within the groups having a BMI<30 (5.0+4.4% vs. 10.9+9.0% respectively p=0.19) and the ones with a BMI>30 (19.4+9.3% vs. 20.8+7.1%, p=0.77). In addition, the statistically significant difference between in intrapancreatic fat between patients with BMI<30 and those with a BMI>30 was maintained irrespective of whether acute pancreatitis was diagnosed on autopsy or by clinical criteria (FIG. 4).

Intrapancreatic fat is higher in patients with clinically severe acute pancreatitis: Of the 13 patients with a clinical diagnosis of acute pancreatitis, 5 had clinically severe acute pancreatitis while 8 had mild acute pancreatitis. The BMI of the patients with clinically severe acute pancreatitis (40.0+ 6.4 vs. 30.3+7.1, p=0.03) (FIG. 5A) as well as the amount of intrapancreatic fat (23.4+9.6%. vs 7.9+5.6%, p=0.003) (FIG. 5B) was significantly higher compared with those who patients mild acute pancreatitis.

Regression analysis reveals BMI as a determinant for intrapancreatic fat: On regression analysis, after controlling for age and disease status (controls vs. acute pancreatitis), a significant positive association was seen between increasing BMI and percent intrapancreatic fat (beta-0.46, p<0.001). In this model, no significant association was seen for intrapancreatic fat with age or disease status.

6.3 Discussion

In this study we have confirmed previous observations that the percentage of intrapancreatic fat increases with BMI in subjects without acute pancreatitis, and extend these findings to patients with acute pancreatitis. In addition, we demonstrate a positive relationship between intrapancreatic fat percentage and the severity of acute pancreatitis. Our observation of an increase in intrapancreatic fat with increasing BMI in subjects without acute pancreatitis is very similar to two recent studies (11, 12). Siasho et al evaluated intrapancreatic fat in subjects without pancreatitis using CT scan and autopsy samples. They calculated fat amount by studying its differential density compared to acinar tissue in the hand outlined pancreas on CT. They included 47 control autopsy patients in whom intrapancreatic fat percentage was compared with BMI, and noted a similar increase in intrapancreatic fat as we do. They also noted an association between increasing intrapancreatic fat and age up to the 4th decade of adult life while studying individuals from birth up to 100 years. 224 of the adults in their study were less than 40 years of age. This age group is not commonly affected by pancreatitis (2/24 acute pancreatitis patients and 5/50 controls in our study) and was not represented in our study, thus contributing the lack of association between intrapancreatic fat and age noted by us. Rosso et al also noted an increase of intrapancreatic fat with BMI, but reported the amount of intrapancreatic fat in deciles. The 4th decile or more (intrapancreatic fat>40%) had a mean BMI of 29.5% 11. Their population of patients, however were post pancreaticoduodenectomy and they did not include patients with acute pancreatitis. A low BMI in their study may have been associated with a previous history of cancer, since 80 of the 111 patients in their study had a duodenal or pancreaticobiliary malignancy, including 61 patients with pancreatic cancer. To our knowledge, the relationship between intrapancreatic fat and BMI in patients with acute pancreatitis has not been evaluated previously. We demonstrate that this relationship in patients with acute pancreatitis is similar to subjects without acute pancreatitis. We found that the intrapancreatic fat percentage in patients with acute pancreatitis was similar to controls—overall or after stratification for BMI. This finding suggests that intrapancreatic fat may not have a causal role in initiating an attack of acute pancreatitis. Of the 13 patients with clinical acute pancreatitis in our study, all 5 patients with severe acute pancreatitis had a BMI of >30. This agrees well with the several studies that have shown an association between obesity and adverse outcomes in patients with acute pancreatitis (Martinez, et al., Pancreatology 2006, 6:206-209; Papachristou, et al., Pancreatology 2006, 6:279-285; Sempere, et al., Pancreatology 2008, 8:257-264; Karimgani, et al., Gastroenterology 1992, 103: 1636-1640). A higher prevalence of obesity in acute pancreatitis patients postmortem is likely due to our use of an autopsy diagnosis of acute pancreatitis which represents a higher percentage of patients dying with severe disease. Moreover, the association between intrapancreatic fat and BMI was significant on linear regression analysis after controlling for age and disease status (i.e. controls vs. acute pancreatitis). While the association of obesity and worse outcomes of acute pancreatitis has been shown in several clinical studies ((Martinez, et al., Pancreatology 2006, 6:206-209; Papachristou, et al., Pancreatology 2006, 6:279-285; Sempere, et al., Pancreatology 2008, 8:257-264; Karimgani, et al., Gastroenterology 1992, 103:1636-1640)), the site/s of fat deposition that may be playing a causal role in this has remained unclear. The significant increase in intrapancreatic fat in obese subjects and with severe acute pancreatitis suggests a potential role of intrapancreatic fat with severity in acute pancreatitis. In our study all 5 of the patients with severe pancreatitis had "extensive" "diffuse" or "widespread" fat necrosis noted in the pancreas at the time of autopsy. Likewise studies in ob/ob mice have shown these to have a fulminant course with high mortality in response to IL-12 and IL-1822. This was associated with severe intrapancreatic fat necrosis, a phenomenon rarely noted in lean mice. Similarly extensive local pancreatic fat necrosis in response to IL-12 and IL-18 was noted in mice with diet induced obesity (Pini, et al, Obesity (Silver Spring) 2009). Whether an increase in intrapancreatic fat is associated with worse intrapancreatic fat necrosis, and if fat necrosis is an innocent bystander or has a pathologic role in pancreatitis remains to be determined. The cause of systemic injury in acute pancreatitis remains unclear. Four of the five patients with severe acute pancreatitis had ARDS/MSOF attributed to pancreatitis. These systemic complications of acute pancreatitis and associated higher mortality have previously been associated with obesity (Papachristou, et al., Pancreatology 2006, 6:279-285; Karimgani, et al., Gastroenterology 1992, 103:1636-1640; Funnell, et al., Br J Surg 1993, 80:484-486; Johnson, et al., Pancreatology 2004, 4:1-6). This has been associated with increased levels of interleukin-la, IL-1 receptor antagonist, Interleukin-6, Interleukin-8 (Sempere, et al., Pancreatology 2008, 8:257-2643). However, whether this is an acute response of intrapancreatic fat to acute pancreatitis or a greater baseline pro-inflammatory state initiated at other sites of visceral fat deposition (Ghanim, et al., Circulation 2004, 110:1564-1571) is unknown. A limitation of our study is the use of autopsy samples. However, biopsies are not routinely performed in patients with acute pancreatitis, making this approach impractical and not feasible. In addition, loss of tissue planes, edema, necrosis during acute pancreatitis and inability to clearly tell intrapancreatic from peripancreatic fat could potentially limit the accuracy of radiologic techniques in determining the amount of intrapancreatic fat during acute pancreatitis. Another limitation of our study is the small sample size, especially for patients with a clinical diagnosis of acute pancreatitis before death. Despite this we note a significant association between intrapancreatic fat amount and BMI with severe acute pancreatitis. Since all patients with clinical acute pancreatitis who had severe acute pancreatitis had a BMI >30, we did not perform a linear regression separately in patients with clinical acute pancreatitis. Our observations should be considered preliminary and will need confirmation in a larger study. In conclusion, the intrapancreatic fat percentage is positively associated with BMI and this relationship is similar in subjects with and without acute pancreatitis. The intrapancreatic fat percentage is also associated with severe acute pancreatitis. The results of our study using an appropriate methodology for measuring intrapancreatic fat in acute pancreatitis patients suggest that intrapancreatic fat may be a potential exacerbating factor in acute pancreatitis, resulting in more severe outcomes. Larger studies and pancreatitis models targeting specifically intrapancreatic fat would be needed to avoid the deficiencies, and understand the mechanisms of the findings mentioned above.

6.4 References

1. Martinez, et al., Obesity is a definitive risk factor of severity and mortality in acute pancreatitis: an updated meta-analysis, Pancreatology 2006, 6:206-209.

2. Papachristou, et al., Obesity increases the severity of acute pancreatitis: performance of APACHE-O score and correlation with the inflammatory response, Pancreatology 2006, 6:279-285.

3. Sempere, et al., Obesity and fat distribution imply a greater systemic inflammatory response and a worse prognosis in acute pancreatitis, Pancreatology 2008, 8:257-264.

4. Karimgani, et al., Prognostic factors in sterile pancreatic necrosis, Gastroenterology 1992, 103:1636-1640.

5. Tsai C J, Is obesity a significant prognostic factor in acute pancreatitis?, Dig Dis Sci 1998, 43:2251-2254.

6. Funnel. et al, Obesity: an important prognostic factor in acute pancreatitis, Br J Surg 1993, 80:484-486.

7. Johnson, et al., Combination of APACHE-II score and an obesity score (APACHE-O) for the prediction of severe acute pancreatitis, Pancreatology 2004, 4:1-6.

8. Ibrahim M M, Subcutaneous and visceral adipose tissue: structural and functional differences, Obes Rev 2009.

9. Park, et al., Visceral adipose tissue area is an independent risk factor for hepatic steatosis, J Gastroenterol Hepatol 2008, 23:900-907.

10. Olsen T S, Lipomatosis of the pancreas in autopsy material and its relation to age and overweight, Acta Pathol Microbiol Scand A 1978, 86A:367-373.

11. Rosso, et al., The role of "fatty pancreas" and of BMI in the occurrence of pancreatic fistula after pancreaticoduodenectomy, J Gastrointest Surg 2009, 13:1845-1851.

12. Saisho, et al., Pancreas volumes in humans from birth to age one hundred taking into account sex, obesity, and presence of type-2 diabetes, Clin Anat 2007, 20:933-942.

13. Schmitz-Moormann, et al., Lipomatosis of the pancreas. A morphometrical investigation, Pathol Res Pract 1981, 173:45-53.

14. Mery, et al., Android fat distribution as predictor of severity in acute pancreatitis, Pancreatology 2002, 2:543-549.

15. Martinez, et al., Obesity: a prognostic factor of severity in acute pancreatitis, Pancreas 1999, 19:15-20.

16. Ghanim, et al., Circulating mononuclear cells in the obese are in a proinflammatory state, Circulation 2004, 110:1564-1571.

17. Mathur, et al., Nonalcoholic fatty pancreas disease, HPB (Oxford) 2007, 9:312-318.

18. Matsumoto, et al., Uneven fatty replacement of the pancreas: evaluation with CT, Radiology 1995, 194:453-458.

19. Kloppel, et al., Chronic pancreatitis: evolution of the disease, Hepatogastroenterology 1991, 38:408-412.

20. Kloppel, et al., Pseudocysts in chronic pancreatitis: a morphological analysis of 57 resection specimens and 9 autopsy pancreata, Pancreas 1991, 6:266-274.

21. Schmitz-Moormann P, Comparative radiological and morphological study of the human pancreas. IV. Acute necrotizing pancreatitis in man, Pathol Res Pract 1981, 171:325-335.

22. Sennello, et al., Interleukin-18, together with interleukin-12, induces severe acute pancreatitis in obese but not in nonobese leptin-deficient mice, Proc Natl Acad Sci USA 2008, 105:8085-8090.

23. Pini. et al., Effect of Diet-induced Obesity on Acute Pancreatitis Induced by Administration of Interleukin-12 Plus Interleukin-18 in Mice, Obesity (Silver Spring) 2009.

7. EXAMPLE

Lipotoxicity Causes Multisystem Organ Failure and Worsens Acute Pancreatitis in Obesity 7.1 Materials and Methods Materials: All reagents were of the highest purity and were procured from Sigma-Aldrich (St. Louis, Mo.) unless otherwise specified. IL-12 was from Peprotech (Rocky Hill, N.J.), IL-18 was from R&D systems (Minneapolis, Minn.), Orlistat was from Cayman Chemical (Ann Arbor, Mich.). Collagenase (type IV) was from Worthington (Lakewood, N.J.). 7-8 week old Female ob-ob (B6.V-Lepob/J) mice, or C57bl6 mice were from Jackson labs (Bar Harbor, Me.) and 150-200 gm Sprague-Dawley rats were from Charles river laboratories (Wilmington, Mass.). All animals were housed with a 12-h light/dark cycle at temperatures from 21-25° C., fed standard laboratory chow, and allowed to drink ad libitum. These were housed for at least 1 week to acclimatize before experimentation. For in vivo, studies there were 8-12 animals per group. All animal experimental protocols were approved by the Institutional Animal Use Committee of the University of Pittsburgh (Pittsburgh, Pa.).

Human Studies:

Collection and analysis of autopsy and clinical data: We searched the University of Pittsburgh Medical Center—Presbyterian Hospital autopsy database from 1998 till 2008 and identified all patients who received a postmortem diagnosis of acute pancreatitis. The diagnosis of acute pancreatitis in all cases was based on gross and microscopic appearance at the time of autopsy. Of the 46 acute pancreatitis patients identified who also had pancreas slides available for review, we excluded the 19 patients in whom the autopsy report also mentioned a pathologic diagnosis of chronic pancreatitis and the two patients who were post Whipple resection for pancreatic cancer to avoid the changes that would occur secondary to these pathologies and do not contribute to mortality in acute pancreatitis. An additional patient with acute pancreatitis whose slides showed severe hemorrhage and excessive autolysis was excluded since this would have precluded an accurate histological assessment. Thus, the total sample size for acute pancreatitis patients was 24. From the remaining patients in the autopsy database, we randomly chose 50 subjects without pancreatitis as controls for this study. There was no significant difference in age, sex or BMI between these or AP cases (Table 1). The slides of all patients and controls were retrieved and reviewed. The study was approved by the Committee for Oversight of Research Involving the Dead and the Institutional Review Board at the University Of Pittsburgh Medical Center.

The electronic medical records of patients with an autopsy diagnosis of acute pancreatitis were reviewed to assess whether a subject met clinical criteria for acute pancreatitis (serum amylase or lipase ≥3 fold upper limit of normal, typical abdominal pain or radiologic findings to support the diagnosis) and to assess the severity acute pancreatitis (defined as presence of single or multisystem organ failure attributable to acute pancreatitis, a mention of necrotizing pancreatitis on computed tomography report, or "widespread", "extensive" or "diffuse" necrosis noted at the time of autopsy). Of the 24 patients, 13 met the clinical criteria for acute pancreatitis. Of these, 1 patient had all 3 criteria (pain, abnormal CT, increased enzymes); 7 patients had 2 criteria (abdominal pain and increased enzymes in 3 patients and CT abnormalities with increased enzymes in 4 patients); 1 had a clinical diagnosis of acute pancreatitis listed on his hospitalization records; 3 were sedated/comatose on ventilator support when elevated pancreatic enzymes (>3fold increase in amylase/lipase) were documented (last week before death); and 1 patient was diagnosed based solely on elevated pancreatic enzymes (this patient also had hypercalcemia during hospital admission). Of the 13 patients, 5 had severe acute pancreatitis based on local complications ("extensive necrosis" or "severe necrotizing pancreatitis", "pancreatic hypoperfusion" mentioned on CT scan, 3 patients; "diffuse" or "extensive" necrosis noted at the time of autopsy, all 5 patients). All 5 patients had acute respiratory distress syndrome, with 4 patients in MSOF, and 4 patients with no previous history of renal disease having an elevated serum BUN and creatinine attributed solely to acute pancreatitis.

The remaining 11 patients did not fulfill the clinical criteria for acute pancreatitis. Nine of these did not have serum amylase or lipase estimation in the 2 weeks prior to death. One patient had a 2-fold elevation 3 days before death (patient had history of alcohol abuse and cirrhosis), and 1 had normal enzymes 5 days before death. CT abdomen was done in only 1 of these 11 patients 9 days before death and was normal. Eight of the patients were on ventilator support 5 or more days before death. Of the remaining 3 patients, one had a history of alcohol abuse as described above, one had septic shock and was on the ventilator for 3 days prior to death (autopsy revealed focal fat necrosis and moderate congestion), and one died of cardiogenic shock in a background of systemic lupus erythematosus (autopsy revealed mild acute pancreatitis). In none of these was pancreatitis thought to be an immediate cause of death. In 1 of the 11 patients, acute pancreatitis was reported as an underlying cause of death. This patient was status post-kidney-pancreas transplant, was on a ventilator for 20 days, and had pulmonary embolism as the immediate cause of death.

For histologic evaluation, we retrieved all hematoxylin and eosin-stained slides of the pancreas (1-4 in number) of control and acute pancreatitis patients. A trained pathologist with specific interest in gastrointestinal pathology blinded to demographic and clinical data examined the slides. Adipose tissue with large vessels and nerves not bounded by at least 2 pieces of pancreatic parenchyma was regarded as peripancreatic and excluded. The remaining adipose tissue, necrotic fat (bluish cheesy appearance of adipocytes), necrotic parenchyma, and parenchymal necrosis immediately contiguous to areas of fat necrosis (peri-fat acinar necrosis; PFAN) were additionally measured. All of these were measured as a percentage pixel area of each individual field after excluding dead space using Adobe Photoshop PS. The pixel areas of individual parameters for each case were added. The final number was divided by the number of fields to give a percentage area for that parameter in the section. For patients with more than 1 section, the average of the percentage of intrapancreatic fat for all fields from different sections was chosen as representative for the specimen. Von Kossa (to study fat necrosis, saponification), TUNEL (Terminal deoxynucleotidyl transferase dUTP nick end labeling), and oil red O staining were done per standard protocol.

Intra-pancreatic fat—CT imaging analysis: Patients who had unenhanced abdominal CT scan prior to their death were identified. The average time between CT study and death was 12±4 days, with a range of 1-45 days. CT scans were acquired with multidetector CT scanners (4-16 detectors) using a slice thickness of 5 mm. CT images were retrieved from the institutional PACS system (iSite 3.5, Philips Healthcare) and de-identified by a certified honest broker. A single reader (A.F.) analyzed the de-identified images using in-house software on a Windows workstation. The reader was blinded to the result of histologic quantification of intra-pancreatic fat.

Adipose tissue presents with characteristic negative (−150 to −30 HU) attenuation on unenhanced CT images. Thus, the attenuation of the pancreas is expected to decrease with fatty infiltration within the pancreas, just as low attenuation of the liver is associated with hepatic steatosis. Two methods were used for CT quantitation of IPF. In method 1, the attenuation of pancreatic parenchyma was measured by placing a total of 9 circular regions of interests (ROIs; 1 cm in maximum diameter) over the head (n=3), body (n=3), and tail (n=3) of the pancreas for each patient (FIG. 11). Blood vessels and pancreatic duct were carefully excluded from ROIs. The mean attenuation of the 9 ROIs was calculated and used for statistical analysis.

In addition to mean attenuation measurements, using a second method (FIG. 6B), the percentage of fat volume within the pancreas was estimated by means of a volumetric histogram and local thresholding method. For this, the boundary of the pancreas on all CT images containing pancreatic parenchyma was delineated to segment the entire pancreatic region. A histogram is calculated from the number and the attenuation values of the pixels of the segmented pancreatic region. The volume of the pancreas was computed as the product of the pixel dimension and the total count of pixels. The volumetric percentage of intra-pancreatic adipose tissue was calculated as the percentage of the number of negative pixels (<0 HU) to the total pixel count.

Pancreatic necrosis surgical debridement fluid analysis: Surgical debridement fluid from 6 patients with pancreatic necrosis was immediately spun at 300 g to remove cellular debris. The supernatant was sonicated and frozen at −80 C for subsequent analysis of non-esterified fatty acids (Gas chromatography, described below).

In vitro studies:

Harvesting cells: Primary acinar cells from wild type mice (C57B6) were harvested and used as described previously. Viability, confirmed by trypan blue exclusion, was >95%. Primary adipocytes were harvested as described previously and exhibited an appropriate lipolysis response to isoproterenol (Isop, 10 µM: FIG. 7). These were used in the individual experiments. Data presented is representative of 3 or more experiments.

Acinar culture: Acinar culture was done as described previously to study inflammatory mediator upregulation.

Figure 17:
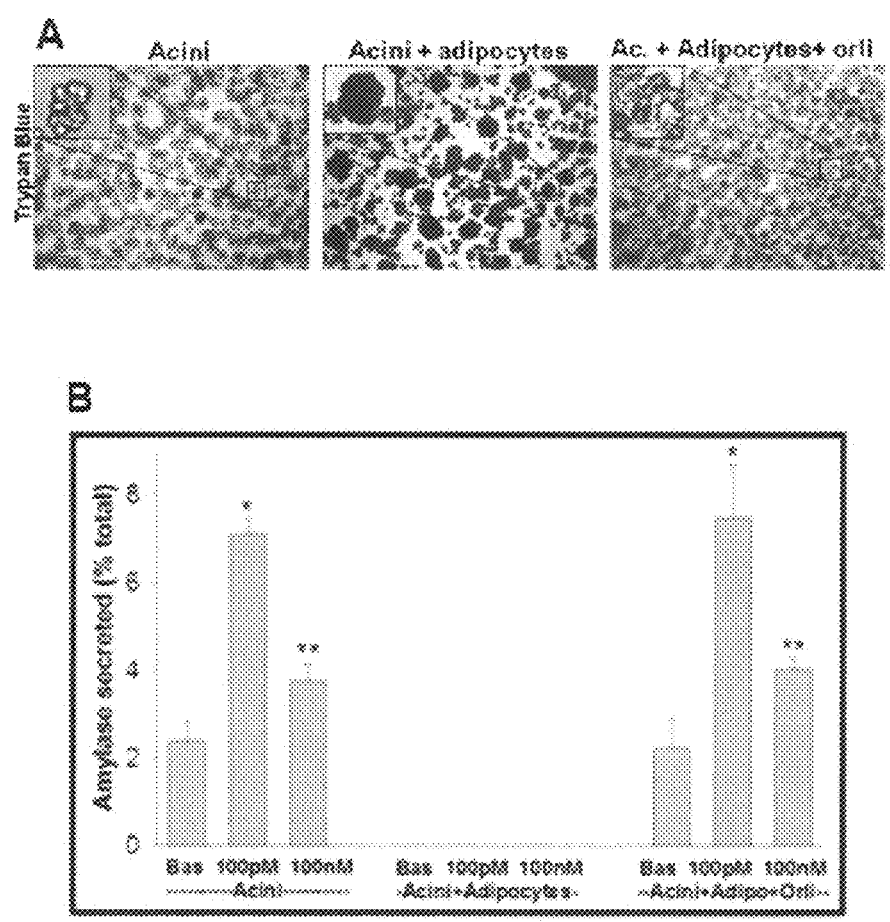

Acinar-adipocyte co-culture: This was done in 12-well companion plates with cell culture inserts (FIG. 14). Acinar cells (20 µl pellet volume per well) and adipocytes 50,000 cell/ml were suspended in the medium (Krebs Ringer HEPES Buffer with 10 mM sodium bicarbonate, pH 7.4 and supplemented with 2.0% fatty acid free albumin) using conditions as described previously. Adipocytes and acinar cells exhibit normal behavior (FIGS. 16, 17) up to 6 hours under these conditions, as do acinar cells separated after being co-cultured in the presence of 50 µM orlistat (FIG. 17).

Serum and medium cytokine assays: These were done for TNF-α, MCP-1, IL-6, resistin, and adiponectin using the fluorescence-based capture sandwich immunoassay based on the Luminex FlowMetrix system (Luminex). The Milliplex Mouse Adipokine Panel (7-Plex) 1 kit from Millipore (Billerica, Mass.) was used. Samples were analyzed using the Bio-Plex suspension array system, which included a fluorescent reader and Bio-Plex Manager analytical software (Bio-Rad Laboratories, Hercules, Calif.) at the University of Pittsburgh, Cancer Institute Luminex Core Facility.

Calcium imaging: Acinar cells loaded with fura-2AM as described previously on 35-mm glass bottom culture dishes (MatTek corporation, Ashland, Mass.) were imaged on temperature-controlled motorized stage of an Olympus IX81 inverted microscope (Olympus America Inc, Melville, N.Y.) with a 20×0.70 NA objective and a QImaging Retiga EXi CCD camera (QImaging, Burnaby, Canada). Baseline images were taken, and cells with extremely bright or dim fluorescence were omitted. Fatty acids (linolenic, linoleic, oleic, stearic, and palmitic, 100-1200 µM final concentration) were added, and cytosolic calcium levels [Cai] were determined by alternate excitation at 340 nm and 380 nm, measuring emission at 510 nm. Pre- and post-images using differential interference contrast were obtained to demonstrate appropriate cell morphology. Image acquisition was with the MetaMorph 7.5 Imaging System (Molecular Devices, Downington, Pa.) using the MetaMorph 6.3 software. The 340/380 emission ratio were averaged for 7-25 acini per field, with background subtraction. Data presented is a mean from separate experiments.

In vivo studies:

Pancreatitis model: IL12+18 model: There were 8-12 animals in each group. Pancreatitis was induced as described previously in 8-10 week old female ob-ob (B6.V-Lepob/J) mice. Briefly, IL-12 (150 ng/dose/mouse) and IL-18 (750 ng/dose/mouse) were simultaneously given intraperitoneally in 2 doses, 24 hours apart. Orlistat at reduced dose than previously published (50 mg/kg) was administered in vehicle (0.1 ml 30% ethanol) as described previously. First injection of orlistat or vehicle was 2 hours after induction of pancreatitis, and these were then repeated every 12 hours.

Other Methods:

Non-esterified fatty acid analysis: The sample was extracted with isopropanol-heptane-hydrochloric acid (1M) (40:10:1, v/v) by vortexing for 25-30 min and allowed to incubate at room temperature for 10 minutes. Heptane (4.0 ml) and water (2.0 ml) were added, and the tubes were thoroughly vortexed for 5 minutes. Tubes were centrifuged at 1000 g for 10 minutes at 4° C., and the upper phase (heptane) is transferred into 13×100 mm screw top tubes and dried in a SpeedVac centrifugal concentrator. Non-esterified fatty acids were derivatized with dimethylamine using the Deoxo-Fluor reagent. Non-esterified fatty acid concentrations are measured by gas chromatography separation with flame ionization detection using heptanoic acid as an internal standard. This derivatization method is very mild and efficient and is selective only towards non-esterified fatty acids so that no separation from a total lipid extract is required.

Visceral fat triglyceride composition: The visceral fat triglyceride composition analysis was done at Kennedy Krieger Institute (Baltimore, Md.). Briefly, total lipids were extracted by the method of Folch. The total lipids were weighed and then separated into 4 fractions by column chromatography on silicic acid. The second fraction has the mono-, di- and triglycerides, the non-esterified fatty acids, and ceramides; 400 micrograms of the second fraction was taken and purified, and non-esterified acids, triglycerides, and diglycerides were collected by thin-layer chromatography on Silica Gel G plates. The fatty acids were derivatized and analyzed by GCMS as their pentafluorbenzylbromide esters. ATP levels, cytochrome C release, and % LDH leakage were measured as previously described. Apoptosis was measured by active caspase-3 [western blotting, activity assays (Enzcheck, Invitrogen, Carlsbad, Calif.)], TUNEL assays, and Hoechst dye nuclear incorporation (8 mg/ml Hoechst 33342 added for 15 minutes after treatment). Apoptotic cells exhibited fragmented or condensed nuclei, whereas necrotic cells did not have significant nuclear changes or had slightly swollen nuclei. Results were reported as % of cells with given nuclear changes. These were counter stained with PI (1 µM) to stain necrotic cells (FIG. 7A, B, C) and imaged with a Zeiss Meta dual fluorescence confocal microscope. PI-positive cells were counted as late apoptosis or necrosis. Decreased ATP levels suggested necrotic cell death. Autophagy was studied by western blotting for LC3-I and II. RNA was extracted using Trizol (Invitrogen, Carlsbad, Calif.). mRNA levels of TNF-α, CXCL1, and CXCL2 were measured as described previously using real time-PCR performed on an ABI Prism 7000 Sequence Detection System (Applied Biosystems, Foster City, Calif.) on proprietary Taqman Gene Expression assay reagents (Applied Biosystems). Mitochondrial complex assays and citrate synthase assay were done as described previously.

Statistical analysis: Continuous data are presented as mean±standard error of mean (SEM) and categorical data as proportions. Bivariate comparisons for continuous data were performed using the Student's t-test or Pearson correlation coefficient, and categorical data were compared using the chi-squared test or Fischer's exact test as applicable. Subjects with a BMI of <30 were classified as normal/overweight while those with a BMI of ≥30 were classified as obese. We used linear regression analyses to determine the factors predicting intrapancreatic fat percentage. In these analyses, we used age (years), BMI (as continuous variable), and disease status (control or acute pancreatitis case) as independent variables. No collinearity was detected on data analysis. A two-tailed p-value of <0.05 was considered as significant. The data were analyzed using SPSS version 17 software, Chicago, Ill.

7.2 Results

IPF in Obesity worsens pancreatic necrosis: Intrapancreatic fat (IPF) levels were found to be positively correlated with BMI irrespective of disease state (FIGS. 6A and 3), as determined by histological assessment or by abdominal CT scans (FIGS. 6B and 11). Patients with SAP had higher BMIs (FIG. 5A) and IPF (FIG. 6A). Pancreatic sections obtained during autopsies of AP patients revealed that pancreatic necrosis occurred predominantly around areas of intrapancreatic fat necrosis (FIGS. 6C, 6C', 6D, 6E, 6F). Obese and SAP patients had more fat necrosis (in quadrangle, staining blue on H&E (FIG. 6C') and dark brown (FIG. 6C) on Von Kossas) and higher peri-fat acinar necrosis (FIGS. 12, 6C, 6C' 6D, 6E, 6F) than non-obese or mild AP and control patients respectively. These changes were unlikely to be a postmortem artifact since autopsy specimens from control patients had insignificant amounts of fat necrosis and acinar necrosis (FIGS. 6D, 6E, 6F, 14). Further support for these changes being antemortem was provided by the finding of CD68-positive macrophage infiltration around fat necrosis but not normal fat (FIG. 13). Von Kossa staining revealed areas of fat necrosis and surrounding peri-fat acinar necrosis to be rich in calcium, suggesting saponification (dashed ovals, FIGS. 6C, 6C') of NEFAs released into the parenchyma. Measurement of NEFA levels in pancreatic necrosis debridement fluid from 6 SAP patients all of who were obese (mean BMI; 36.7±4.7) showed a mean concentration of 7.8±2.9 mM of which 75.3% were unsaturated fatty acids (FIG. 6G), with NEFA concentrations as high as 65 mM being present in debridement tissue homogenates.

Figure 15:
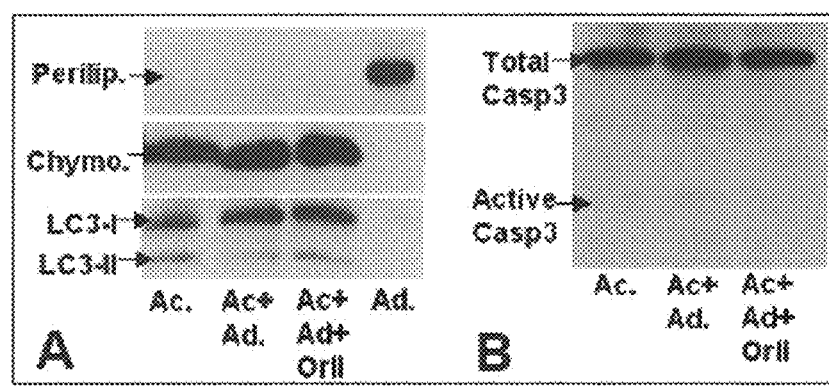

Lipolysis regulates necrosis, resistin levels: Disruption of the apically directed polarized trafficking results in basolateral leakage of enzymes and other macromolecules during pancreatitis (11 (reference 11, listed in section 7.4 below)). Since this macromolecular diffusion may play a role in fat-induced acinar necrosis, we simulated the pathological leakage by co-culturing adipocytes and pancreatic acini (FIG. 14). There was no contamination of one cell type by the other. When individually cultured, each cell type appeared morphologically and physiologically normal. However, co-culture resulted in acinar cell necrosis as evidenced by propidium iodide positivity, drop in ATP levels and cytochrome c leakage (FIGS. 7A-F) in the absence of increased active caspase-3 or increase in LC3-II (FIG. 15). These changes in acinar cells were accompanied by a large increase in NEFA concentrations (FIG. 7G) and resistin in the medium (FIG. 18), which was similar to that observed in debridement fluid (FIG. 6G) and serum, respectively, of patients with severe AP7. All of these changes in acinar cells were completely prevented by inhibiting lipase using orlistat (50 μM), which restored acinar cell viability and function to control levels (FIGS. 7C-G, 16, 17, 18).

UFAs induce necrosis and are proinflammatory: To determine the fatty acids causing acinar cell necrosis in co-culture, we exposed acinar cells to individual fatty acids at concentrations less than or equal to those in co-culture or debridement fluid. Intracellular calcium levels increased with unsaturated fatty (FIG. 8A), which came from an intracellular pool since it was inhibited by thapsigargin, but not by the extracellular calcium chelator EGTA (FIG. 8B). UFAs also caused LDH leakage into the medium (FIGS. 8C, 19A). Both the LDH leakage and intracellular calcium increase were dose dependent (FIGS. 8C, 19B). Chelation of the intracellular pool with BAPTA partially prevented LDH leakage and cytochrome C release although this protection was not sustained beyond 3 hours (FIG. 20). Linoleic acid (300 μM) but not palmitic acid (1200 μM) inhibited mitochondrial complexes I and V (FIGS. 8D, 8E, 21), causing a drop in ATP levels and necrotic cell death (FIG. 22). Additionally, sub-lethal concentrations (200 μM) of linoleic acid (which increase cytosolic Ca) but not palmitic acid increased acinar mRNA levels of TNF-α, and the neutrophil chemoattractants CXCL1 and CXCL2 (FIGS. 8F, 8G, 8H).

Lipolysis contributes to pancreatic necrosis: Ob/ob mice developed pancreatitis in response to IL12 and 18 that was associated with an increase in serum amylase and lipase levels (FIG. 23). Pancreata of ob/ob mice contained 26±2.1% fat. Von Kossa staining revealed areas of fat necrosis, saponification (FIGS. 9A, 9F) and surrounding peri-fat acinar necrosis (FIGS. 9A', 9G) to contribute significantly to total acinar necrosis (FIGS. 9A', 9E). Grossly, pancreata of mice with pancreatitis had saponification, seen as chalky deposits (FIG. 9B), which also were scattered throughout the fat in the peritoneal cavity (FIG. 9C) with associated hypocalcemia (FIG. 9D). Orlistat treatment significantly blocked all these changes observed in ob/ob with pancreatitis on gross (FIGS. 9B', 9C'), histologic (FIGS. 9A', 9E, 9F, 9G) and biochemical (FIG. 9D) evaluation.

Figure 10M:
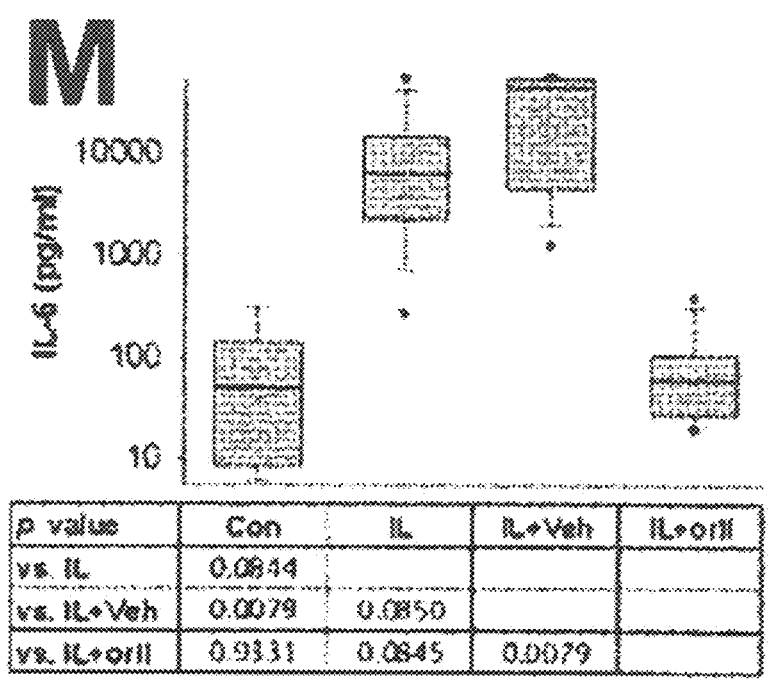

Lipotoxicity results in MSOF: Evaluation of the triglyceride composition of visceral adipose tissue showed UFAs to be significantly increased in obese mice (73% vs 48%, p=0.003) compared to lean mice (FIG. 10A), with a corresponding decrease in SFAs. Pancreatitis resulted in a significant increase in serum UFA levels and mortality, both of which were significantly reduced in orlistat-treated animals (FIGS. 10B, 10C). SFA levels were not significantly reduced by orlistat (FIG. 24). End organ damage in ob/ob mice included renal failure with high BUN levels (FIG. 10G), renal tubular vacuoles (FIGS. 10D1, 10D2) positive for fat on oil red O (FIG. 10E1, 10E2), tubular apoptosis and injury (TUNEL positive, FIGS. 10F1, 10F2), mitochondrial swelling and saponification (FIG. 25A-D). Tubular damage was also noted in autopsies of SAP patients with acute renal failure (FIGS. 25E, 25F). All of these changes were normalized in the orlistat treated animals (FIGS. 10D3, 10E3, 10F3) to levels similar to controls (FIGS. 10D, 10E, 10F). Lung injury, similar to oleic acid infusion induced injury (12); manifested as increased apoptotic cells (FIGS. 10H, 26B, 26C) and lung MPO levels (FIG. 10I) were also significantly reduced in the orlistat treated group (FIGS. 10H, 10I, 26D). Furthermore, orlistat also normalized serum resistin, TNF-α, MCP-1 and IL-6 (FIGS. 10J, 10K, 10L, 10M), suggesting reduction in systemic inflammation.

7.3 Discussion

We show here that local and systemic lipotoxicity contributes to multisystem organ failure and worse outcomes in obese patients and mice with pancreatitis. We show that these effects maybe due to UFAs generated locally that induce necrotic cell death via intracellular calcium release and inhibition of mitochondrial complexes I and V. UFAs also upregulate inflammatory mediators at sub-lethal concentrations. Inhibition of lipolysis in vitro and in vivo inhibits resistin and inflammatory mediator generation. Additionally, there was accumulation of oil red O positive vacuoles in renal tubules with mitochondrial swelling, tubular injury and saponification in the kidneys of mice and patients dying with renal failure. Thus the 2 modes of systemic lipotoxicity seem to be a direct cellular toxicity, and an indirect one via upregulating other inflammatory mediators (e.g. TNF-α) which may worsen local and systemic injury independently.

UFAs comprised 73-75% of the human pancreatitis debridement fluid and visceral adipose triglyceride content of obese mice vs. 48% in lean mice. Therefore, this 1.5 fold UFA increase, combined with the two fold increase in intrapancreatic fat with obesity (10.4+1.6% in BMI<30 vs. 19.4+1.6% in BMI>30, p=0.009) (FIG. 6A) can potentially result in a three fold increase in UFA concentrations when lipolysis is initiated, sufficient to cause local and systemic lipotoxicity. While the increase in serum UFAs with pancreatitis and decrease with orlistat treatment were significant (FIG. 10B), the smaller magnitude of these changes noted compared to other parameters may be due to their saponification and renal excretion, eventually resulting in tubular toxicity (13). Additionally, the more impressive systemic and in vitro effects of orlistat compared to the local pancreatic effects may be due to its limited permeability across membranes (FIG. 16), which could have reduced entry into pancreatic tissue.

Our findings have broad relevance since worse outcomes associated with elevated serum NEFAs have been noted in patients with severe burns, trauma, acute pancreatitis and other critical illness (14,15). Interestingly, elevated serum lipase levels and increased serum UFA/SFA ratios have also been associated with worse outcomes in these conditions (15,16). Our studies suggest that the UFAs generated from lipolysis contribute to the inflammation, necrosis, MSOF and mortality in obesity and inhibition of lipolysis reduces all these. UFAs administered through various routes have replicated individual parts of the pathophysiology of MSOF, further supporting our conclusions. Dettlebach et al noted hypocalcemia and intraperitoneal saponification by intraperitoneal instillation of oleic or linoleic but not palmitic or stearic acid (17). Oleic acid administered intravenously at concentrations found in our study results in ARDS with lung MPO increase and TUNEL positivity (12). Oleic acid and linoleic acid injected into the pancreatic duct induce pancreatitis (18). Similarly UFAs can elevate serum creatinine (17) and cause renal tubular toxicity (19).

TABLE 1

Table comparing the Age, Sex, BMI of autopsy cases (50 controls and 24 AP cases). Values shown are means ± standard deviation. There was no significant difference between the two groups.

|  | Controls | AP | p value |
|---|---|---|---|
| Age (Years) (Mean +/− SD) | 64 ± 16 | 59 ± 15 | 0.221 |
| Sex (F:M) | 23:27 | 6:18 | 0.126 |
| BMI (mean +/− SD) | 30.2 ± 8.1 | 33.3 ± 8.5 | 0.130 |

7.4 REFERENCES

1. A. M. Ghanem, S. Sen, B. Philp et al., *Burns* 37 (2), 208; A. L. Neville, C. V. Brown, J. Weng et al., *Arch Surg* 139 (9), 983 (2004).
2. D. J. Ciesla, E. E. Moore, J. L. Johnson et al., *Journal of the American College of Surgeons* 203 (4), 539 (2006).
3. H. Oliveros and E. Villamor, *Obesity* (Silver Spring, Md. 16 (3), 515 (2008).
4. G. I. Papachristou, D. J. Papachristou, H. Avula et al., *Pancreatology* 6 (4), 279 (2006).
5. K. A. Porter and P. A. Banks, *Int J Pancreatol* 10 (3-4), 247 (1991).
6. P. Heiss, T. Bruennler, B. Salzberger et al., *Pancreatology* 10 (6), 726; S. S. Vege, T. B. Gardner, S. T. Chari et al., *The American journal of gastroenterology* 104 (3), 710 (2009).
7. A. Schaffler, 0. Hamer, J. Dickopf et al., *The American journal of gastroenterology*.
8. Y. Saisho, A. E. Butler, J. J. Meier et al., *Clin Anat* 20 (8), 933 (2007).
9. J. A. Sennello, R. Fayad, M. Pini et al., *Proceedings of the National Academy of Sciences of the United States of America* 105 (23), 8085 (2008).
10. M. Pini, J. A. Sennello, R. J. Cabay et al., *Obesity* (Silver Spring, Md. (2009).
11. G. Kloppel, T. Dreyer, S. Willemer et al., *Virchows Archiv* 409 (6), 791 (1986).
12. N. Hussain, F. Wu, L. Zhu et al., *American journal of respiratory cell and molecular biology* 19 (6), 867 (1998); J. P. Lai, S. Bao, I. C. Davis et al., *British journal of pharmacology* 156 (1), 189 (2009).
13. L. Hagenfeldt, *Clinica chimica acta; international journal of clinical chemistry* 32 (3), 471 (1971); A. Kamijo, K. Kimura, T. Sugaya et al., *Kidney international* 62 (5), 1628 (2002).
14. M. G. Jeschke, C. C. Finnerty, G. A. Kulp et al., *Pediatr Crit Care Med* 9 (2), 209 (2008); M. G. Jeschke, D. Klein, and D. N. Herndon, *Annals of surgery* 239 (4), 553 (2004); S. Domschke, P. Malfertheiner, W. Uhl et al., *Int J Pancreatol* 13 (2), 105 (1993).
15. K. Sztefko and J. Panek, *Pancreatology* 1(3), 230 (2001); P. E. Cogo, G. Giordano, T. Badon et al., *Pediatric research* 41 (2), 178 (1997).
16. D. J. Malinoski, P. Hadjizacharia, A. Salim et al., *The Journal of trauma* 67 (3), 445 (2009); J. Manjuck, J. Zein, C. Carpati et al., *Chest* 127 (1), 246 (2005); C. M. Ryan, R. L. Sheridan, D. A. Schoenfeld et al., *Annals of surgery* 222 (2), 163 (1995).
17. M. A. Dettelbach, L. J. Deftos, and A. F. Stewart, *J Bone Miner Res* 5 (12), 1249 (1990).
18. S. Willemer, H. P. Elsasser, H. F. Kern et al., *Pancreas* 2 (6), 669 (1987).
19. D. A. Ishola, Jr., J. A. Post, M. M. van Timmeren et al., *Kidney international* 70 (4), 724 (2006); J. H. Moran, G. Nowak, and D. F. Grant, *Toxicology and applied pharmacology* 172 (2), 150 (2001).
20. J. E. Everhart, CE Ruhl, *Gastroenterol.* 136, 376 (2009).
21. W. Kimura, F Meyer, D. Hess, T. Kirchner, W. Fischbach, J. Mossner, *Gastroenterol.* 103, 1916 (1992).
22. F. Paye, O. Presset, J. Chariot, G. Molas, C. Roze, *Pancreas* 23, 341 (2001).

8. EXAMPLE

Lipase Inhibitors for the Treatment of Pancreatitis and Organ Failure 8.1 Background Experiments were performed using a model, the technique of which is established and well described in rats (1, 2, 4, 7). This involves infusion of agents into the pancreatic duct to cause acute pancreatitis (1, 2, 4, 7). We will refer to this technique as "intraductal infusion". We compared the severity of pancreatic damage and survival of rats after intraductal infusion of Glyceryl trilinoleate with and without the lipase inhibitor orlistat. In addition, we used a different lipase inhibitor-cetilistat (3, 6), and studied its efficacy in improving survival of rats in intraductal infusion pancreatitis induced with Glyceryl trilinoleate (GTL).

8.2 Methods

Male Wistar rats (250-350 gm), were anesthetized. Intraductal infusion of 0.1 ml (n=5) or 0.2 ml (n=5) of GTL (Sigma-Aldrich corporation) alone or GTL+orlistat (Caymen chemical, Ann Arbor, Mich.) (75 mg/ml, 0.1 ml n=5 or 0.2 ml n=5) or GTL+cetilistat (Jinan Wedo Industrial Co., Ltd., Jinan City, Shandong China) (25 mg/ml, 0.2 ml, n=10) was done as described previously (1, 2, 4, 7). All animals were given pain control (buprenorphine 200 mcg/kg BID), Cefazolin (100 mg/kg), and 10 cc saline subcutaneously BID as per the IACUC protocol. These were followed for survival.

8.3 Results

Gross pancreatic appearance: Intraductal GTL caused severe hemorrhages, and near total necrosis of the gland within 24 hours. Orlistat and cetilistat prevented the hemorrhages and necrosis up to 5 days. Representative images from 8 rats from each group are shown in FIG. 27A-C.

Mortality: All animals with intraductal infusion of GTL without further treatment were dead in less than 24 hours (first day mortality 10/10). All animals with GTL+orlistat survived up to day 5 (day 5 mortality, 0/10). 2 out of the 10 animals with GTL+cetilistat died over the 5 day period (day 5 mortality 2/10). This is summarized in TABLE 2, below.

TABLE 2

| Agent | mortality | Significance vs. GTL alone |
|---|---|---|
| GTL | 10/10 | |
| GTL + orlistat | 0/10 | P = 0.0001 (Fisher exact test) |
| GTL + Cetilistat | 2/10 | P = 0.0007 (Fisher exact test) |

Lung injury: GTL treated rats had numerous apoptotic cells present in the lungs at the time of necropsy. This was shown by TUNEL staining FIG. 29A shows a representative lung image from such an animal with arrows pointing towards the brown staining TUNEL positive nuclei. Orlistat or cetilistat in combination with GTL nearly completely prevented the lung injury as noted by near absence of such TUNEL positive nuclei at the time of necropsy as shown in FIG. 28B and FIG. 28C respectively.

Renal injury: GTL treated rats had numerous apoptotic cells present in the kidneys at the time of necropsy. This was shown by TUNEL staining FIG. 29A shows a representative kidney image from such an animal with numerous brown staining TUNEL positive nuclei in the renal tublules. Orlistat or cetilistat in combination with GTL nearly completely prevented the renal injury as noted by near absence of such TUNEL positive nuclei at the time of necropsy as shown in FIG. 29B and FIG. 29C respectively.

8.4 DISCUSSION

1. Lipase inhibition with orlistat reduces the severity, prevents multisystem organ failure and improves survival in mechanistically dissimilar models of pancreatitis. Our previous study showed the benefits of using orlistat to inhibit lipases which improved the above in IL12+IL18 induced pancreatitis(5). With the above data we show its benefits in an intraductal infusion model if acute pancreatitis.
2. Inhibiting lipases improves survival in acute pancreatitis. Since both lipase inhibitors cetilistat and orlistat improved survival in the data shown above, the benefit of lipase inhibition in improving survival in acute pancreatitis is not agent specific but can be achieved from using different pharmacologic agents that inhibit lipases. This lipase inhibitors as a class of drugs may improve outcomes in acute pancreatitis.

8.5 REFERENCES

1. Aho H J, Koskensalo S M, and Nevalainen T J. Experimental pancreatitis in the rat. Sodium taurocholate-induced acute haemorrhagic pancreatitis. Scandinavian journal of gastroenterology 15: 411-416, 1980.
2. Anderson R J, Jeffrey I J, Kay P M, and Braganza J M. Peroxidised linoleic acid and experimental pancreatitis. Int J Pancreatol 1: 237-248, 1986.
3. Bryson A, de la Motte S, and Dunk C. Reduction of dietary fat absorption by the novel gastrointestinal lipase inhibitor cetilistat in healthy volunteers. British journal of clinical pharmacology 67: 309-315, 2009.
4. Kataoka K, Sasaki T, Yorizumi H, Sakagami J, and Kashima K. Pathophysiologic studies of experimental chronic pancreatitis in rats induced by injection of zein-oleic acid-linoleic acid solution into the pancreatic duct. Pancreas 16: 289-299, 1998.
5. Navina S, Acharya C, DeLany J P, Orlichenko L S, Baty C J, Shiva S S, Durgampudi C, Karlsson J M, Lee K, Bae K T, Furlan A, Behari J, Liu S, McHale T, Nichols L, Papachristou G I, Yadav D, and Singh V P. Lipotoxicity causes multisystem organ failure and exacerbates acute pancreatitis in obesity. Science translational medicine 3: 107ra110.H
6. Padwal R. Cetilistat, a new lipase inhibitor for the treatment of obesity. Curr Opin Investig Drugs 9: 414-421, 2008.
7. Zhu Z H, Holt S, el-Lbishi M S, Grady T, Taylor T V, and Powers R E. A somatostatin analogue is protective against retrograde bile salt-induced pancreatitis in the rat. Pancreas 6: 609-613, 1991.

9. EXAMPLE

Improved Orlistat Formulation 9.1 Background

Due to solubility issues orlistat precipitates in an aqueous environment, limiting the modes by which it may be administered. Formulations to make orlistat stay in solution in an aqueous environment are either in free (also called non esterified) fatty acids or polyethylene glycol. Since free fatty acids are toxic and cause/worsen pancreatitis themselves (Navina S, Acharya C, DeLany J P, Orlichenko L S, Baty C J, Shiva S S, Durgampudi C, Karlsson J M, Lee K, Bae K T, Furlan A, Behari J, Liu S, McHale T, Nichols L, Papachristou G I, Yadav D, and Singh V P. Lipotoxicity causes multisystem organ failure and exacerbates acute pancreatitis in obesity. *Science translational medicine* 3: 107ra110) and polyethylene glycol, which also is potentially toxic reduces the potency of orlistat, we therefore have developed a new formulation of orlistat which does not have these issues. We also show that this formulation improves the outcomes in a lethal model of pancreatitis-caerulin in obese mice.

9.2 Methods

Solution of orlistat (Called agent B): To make 7.5 mls of the orlistat solution (called agent B), 75 mg of orlistat was weighed to which 187 microliters of glyceryl trilinoleate (GTL) was added, and the mixture was gently heated to for 15-30 seconds, with gentle shaking till clear. 3.75 mgs of sodium taurocholate was dissolved in 7.2 ml saline (phosphate buffered, with a pH of 7.4) in a separate container. The sodium taurocholate solution was added gradually in small (about 1 ml) aliquots to the orlistat GTL solution, and sonicated after the addition of one or each of these. This resulted in a white solution. The solution when spun at 100 g for 2 minutes, did not result in precipitation of the orlistat and was stable at 4 C for at least 2 weeks. This solution of orlistat was called agent B.

Solution without orlistat (called agent A). The solution resulting from the omission of orlistat form the above process was called Agent A.

Model of pancreatitis: 50-55 gm ob/ob mice were given an injection of caerulein (50 mcg/kg) every hour for 12 hours on 2 consecutive days.
Treatment groups (5 animals/group):
1. pancreatitis alone
2. Pancreatitis with agent A (0.25 ml given intraperitoneally 30 minutes before first caerulein injection and 12 hourly thereafter)
3. Pancreatitis with agent B (0.25 ml given intraperitoneally 30 minutes before first caerulein injection and 12 hourly thereafter)
9.3 Results Mortality: 5/5 untreated animals with pancreatitis died (100% mortality, median second day). 5/5 animals with pancreatitis and agent A died (100% mortality, median second day). 1/5 animals with pancreatitis and agent B died (20% mortality, third day). The reduction in pancreatitis mortality with agent B was significant (p=0.0476). This is shown in TABLE 3 below.

TABLE 3

| condition | mortality | P value vs. pancreatitis + agent B |
|---|---|---|
| controls | 0/8 (0%) | 0.3846 |
| Pancreatitis | 5/5 (100%) | 0.0476 |
| Pancreatitis + agent A | 5/5 (100%) | 0.0476 |
| Pancreatitis + agent B | 1/5 (20%) | |

Hypocalcemia: Agent B significantly prevented hypocalcemia induced by pancreatitis. As shown in TABLE 4 below.

TABLE 4

| condition | Mean Serum calcium (mg/dl) | P value vs. pancreatitis + agent B |
|---|---|---|
| controls | 9.5 | 0.11 |
| Pancreatitis | 4.9 | 0.005 |
| Pancreatitis + agent A | 2.9 | 0.0002 |
| Pancreatitis + agent B | 11.8 | |

CONCLUSIONS

1. The proposed formulation of orlistat is stable in aqueous form and efficacious in reducing the adverse outcomes and mortality of a lethal model of pancreatitis.

2. We have so far shown the efficacy of lipase inhibition in improving outcomes in IL12+IL18 induced pancreatitis and GTL induced pancreatitis. The above data is also a third mechanistically distinct model (caerulein on obese mice) showing the efficacy of lipase inhibitors in the treatment of severe acute pancreatitis.

Various publications are cited herein which are hereby incorporated by reference in their entireties.

What is claimed is:

1. A liquid pharmaceutical composition comprising an effective amount of a lipase inhibitor selected from the group consisting of orlistat, cetilistat, and a combination thereof, a triglyceride form of one or more fatty acid selected from the group consisting of oleic acid, linoleic acid, palmitic acid, and stearic acid, and a bile salt selected from the group consisting of taurocholate, a salt of a cholic acid, and a salt of a glycine conjugate of a cholic acid, and combinations thereof; where the triglyceride form of one or more fatty acid and the bile salt are present in amounts that enhance the solubility of the lipase inhibitor in the composition.

2. The pharmaceutical composition of claim 1 where the lipase inhibitor is orlistat.

3. The pharmaceutical composition of claim 1 where the lipase inhibitor is cetilistat.

4. The pharmaceutical composition of claim 1 where the triglyceride form of one or more fatty acid is glyceryl trilinoleate.

5. The pharmaceutical composition of claim 2 where the triglyceride form of one or more fatty acid is glyceryl trilinoleate.

6. The pharmaceutical composition of claim 3 where the triglyceride form of one or more fatty acid is glyceryl trilinoleate.

7. The pharmaceutical composition of claim 1 where the bile salt is sodium taurocholate.

8. The pharmaceutical composition of claim 2 where the bile salt is sodium taurocholate.

9. The pharmaceutical composition of claim 3 where the bile salt is sodium taurocholate.

10. The pharmaceutical composition of claim 4 where the bile salt is sodium taurocholate.

11. The pharmaceutical composition of claim 5 where the bile salt is sodium taurocholate.

12. The pharmaceutical composition of claim 6 where the bile salt is sodium taurocholate.

* * * * *

UNITED STATES PATENT AND TRADEMARK OFFICE
CERTIFICATE OF CORRECTION

PATENT NO. : 9,943,499 B2  
APPLICATION NO. : 14/677770  
DATED : April 17, 2018  
INVENTOR(S) : Vijay Prem Singh Page 1 of 1

It is certified that error appears in the above-identified patent and that said Letters Patent is hereby corrected as shown below:

In the Specification

Column 1, Lines 16-20 should read:
-- This invention was made with government support under grant numbers RR024153 and DK092460 awarded by the National Institutes of Health. The government has certain rights in the invention. --

Signed and Sealed this
Twelfth Day of February, 2019

Andrei Iancu
*Director of the United States Patent and Trademark Office*